United States Patent
Singh

(10) Patent No.: US 8,934,839 B2
(45) Date of Patent: Jan. 13, 2015

(54) METHODS AND APPARATUS TO CONNECT WIRELESS-ENABLED DEVICES

(75) Inventor: Jasjit Singh, New Delhi (IN)

(73) Assignee: BlackBerry Limited, Waterloo, Ontario (CA)

( * ) Notice: Subject to any disclaimer, the term of this patent is extended or adjusted under 35 U.S.C. 154(b) by 196 days.

(21) Appl. No.: 13/635,326

(22) PCT Filed: Feb. 22, 2011

(86) PCT No.: PCT/US2011/025720
§ 371 (c)(1),
(2), (4) Date: Sep. 14, 2012

(87) PCT Pub. No.: WO2012/115625
PCT Pub. Date: Aug. 30, 2012

(65) Prior Publication Data
US 2013/0005266 A1    Jan. 3, 2013

(51) Int. Cl.
| | |
|---|---|
| *H04B 7/00* | (2006.01) |
| *H04L 29/06* | (2006.01) |
| *H04M 1/67* | (2006.01) |
| *H04M 1/725* | (2006.01) |
| *H04W 8/00* | (2009.01) |
| *A61B 5/00* | (2006.01) |

(Continued)

(52) U.S. Cl.
CPC ........ *H04L 63/0861* (2013.01); *H04L 63/0428* (2013.01); *H04L 63/0442* (2013.01); *H04M 1/67* (2013.01); *H04M 1/7253* (2013.01); *H04W 8/005* (2013.01); *A61B 5/0022* (2013.01); *A61B 5/0024* (2013.01); *A61B 5/024* (2013.01); *H04L 63/101* (2013.01); *H04M 2250/12* (2013.01); *H04L 67/12* (2013.01)
USPC ........................ 455/41.2; 455/39; 340/539.12

(58) Field of Classification Search
CPC . G06F 19/3418; A61B 5/0002; A61B 5/0022
USPC ................. 455/39, 41.2; 340/539.11, 539.12; 600/300; 607/60
See application file for complete search history.

(56) References Cited

U.S. PATENT DOCUMENTS

| | | | |
|---|---|---|---|
| 6,558,320 B1 * | 5/2003 | Causey et al. ................. | 600/300 |
| 6,774,796 B2 | 8/2004 | Smith | |
| 7,043,305 B2 * | 5/2006 | KenKnight et al. ............. | 607/60 |

(Continued)

FOREIGN PATENT DOCUMENTS

WO     2009/032134     3/2009

OTHER PUBLICATIONS

Patent Cooperation Treaty, "International Search Report," issued by the International Searching Authority in connection with PCT application No. PCT/US2011/025720, mailed Dec. 6, 2011 (4 pages).

(Continued)

*Primary Examiner* — Sonny Trinh
(74) *Attorney, Agent, or Firm* — Hanley, Flight and Zimmerman, LLC

(57) ABSTRACT

Example methods and apparatus to connect wireless-enabled devices are disclosed. A disclosed example method involves collecting first biophysical signal data via a first wireless-enabled device and establishing a wireless connection between the first wireless-enabled device and a second wireless-enabled device based on a comparison of the first biophysical signal data and second biophysical signal data collected at the second wireless-enabled device.

24 Claims, 9 Drawing Sheets

(51) Int. Cl.
*A61B 5/024* (2006.01)
*H04L 29/08* (2006.01)

(56) References Cited

U.S. PATENT DOCUMENTS

| | | | | |
|---|---|---|---|---|
| 7,058,453 | B2* | 6/2006 | Nelson et al. | 607/60 |
| 7,171,177 | B2 | 1/2007 | Park et al. | |
| 7,181,505 | B2* | 2/2007 | Haller et al. | 709/219 |
| 7,324,850 | B2* | 1/2008 | Persen et al. | 607/30 |
| 7,353,063 | B2* | 4/2008 | Simms, Jr. | 607/32 |
| 7,782,193 | B2* | 8/2010 | Goh et al. | 340/539.12 |
| 7,859,401 | B2* | 12/2010 | Falck et al. | 340/539.12 |
| 7,978,062 | B2* | 7/2011 | LaLonde et al. | 340/539.11 |
| 7,978,063 | B2* | 7/2011 | Baldus et al. | 340/539.12 |
| 8,587,427 | B2* | 11/2013 | LaLonde et al. | 340/539.12 |
| 2009/0118595 | A1* | 5/2009 | Greiner et al. | 600/301 |
| 2010/0009628 | A1 | 1/2010 | Hebiguchi | |
| 2010/0113950 | A1 | 5/2010 | Lin et al. | |
| 2011/0221590 | A1* | 9/2011 | Baker et al. | 340/539.12 |

OTHER PUBLICATIONS

Patent Cooperation Treaty, "Written Opinion of the International Searching Authority," issued by the International Searching Authority in connection with PCT/US2011/025720, mailed Dec. 6, 2011 (7 pages).

Poon et al., "A Novel Biometrics Method to Secure Wireless Body Area Sensor Networks for Telemedicine and M-Health," IEEE Communications Magazine, Apr. 2006, 9 pages.

Bao et al., "Physiological Signal Based Entity Authentication for Body Area Sensor Networks and Mobile Healthcare Systems," Engineering in Medicine and Biology Society, 2005, 4 pages.

Bao et al., "Using the Timing Information of Heartbeats as an Entity Identifier to Secure Body Sensor Network," IEEE Transactions on Information Technology in Biomedicine, vol. 12, No. 6, Nov. 2008, 8 pages.

Ullah et al., "On PHY and MAC Performance in Body Sensor Networks," EURASIP Journal on Wireless Communications and Networking, May 14, 2009, 7 pages.

Strogatz et al., "Coupled Oscillators and Biological Synchronization," Scientific American, Dec. 1993, 7 pages.

Tulyakov et al., "Identification Model with Independent Matching Scores," The Biometric Consortium Conference, Sep. 19-21, 2005, Arlington, VA, USA, [retrieved from http://www.biometrics.org/bc2005/Presentations/Conference/1%20Monday%20September%2019/Poster%20Session/Govindaraju_identification_model.pdf] 2 pages.

Deliot et al., "Self-Stabilizing Pulse Synchronization Inspired by Biological Pacemaker Networks," Mar. 13, 2003, 31 pages.

Patent Cooperation Treaty, "International Preliminary Report on Patentability," issued by the International Bureau in connection with PCT application No. PCT/US2011/025720, mailed Aug. 27, 2013 (6 pages).

\* cited by examiner

METHODS AND APPARATUS TO CONNECT WIRELESS-ENABLED DEVICES

RELATED APPLICATION

This is a U.S. national phase application under 35 USC 371 of International Application No. PCT/US2011/025720, filed on Feb. 22, 2011, which is hereby incorporated herein by reference in its entirety.

FIELD OF THE DISCLOSURE

The present disclosure relates generally to mobile communication devices and, more particularly, to methods and apparatus to connect wireless-enabled devices.

BACKGROUND

Wireless radio communication technologies are used in many devices to enable such devices to establish wireless connections with one another. Such wireless radio communication technologies include Bluetooth® wireless technology, IEEE® 802.11 wireless technology, and other wireless technologies capable of short-range wireless connections. Known techniques for establishing wireless connections between devices typically require users to enter passwords or pass codes and/or perform other user entry operations prior to making a successful connection to ensure that the connection is intended and that the user is aware of and consents to the connection being established. For example, synching or pairing of phones, smart phones, or other devices over wireless connections (e.g., Bluetooth® wireless connections) using known techniques involves a user-driven process in which a user is heavily involved throughout the process of establishing a connection. For example, user involvement in such known techniques for enabling Bluetooth® radios and/or other wireless technology radios to synch or connect mobile devices typically require users to activate a connecting/pairing process, initiate discovery of devices, and select discovered devices with which to connect. After a user has successfully navigated through several graphical user interfaces, provided the correct information, and made a number of selections, a wireless connection between two devices may be established.

DETAILED DESCRIPTION

Figure 1:
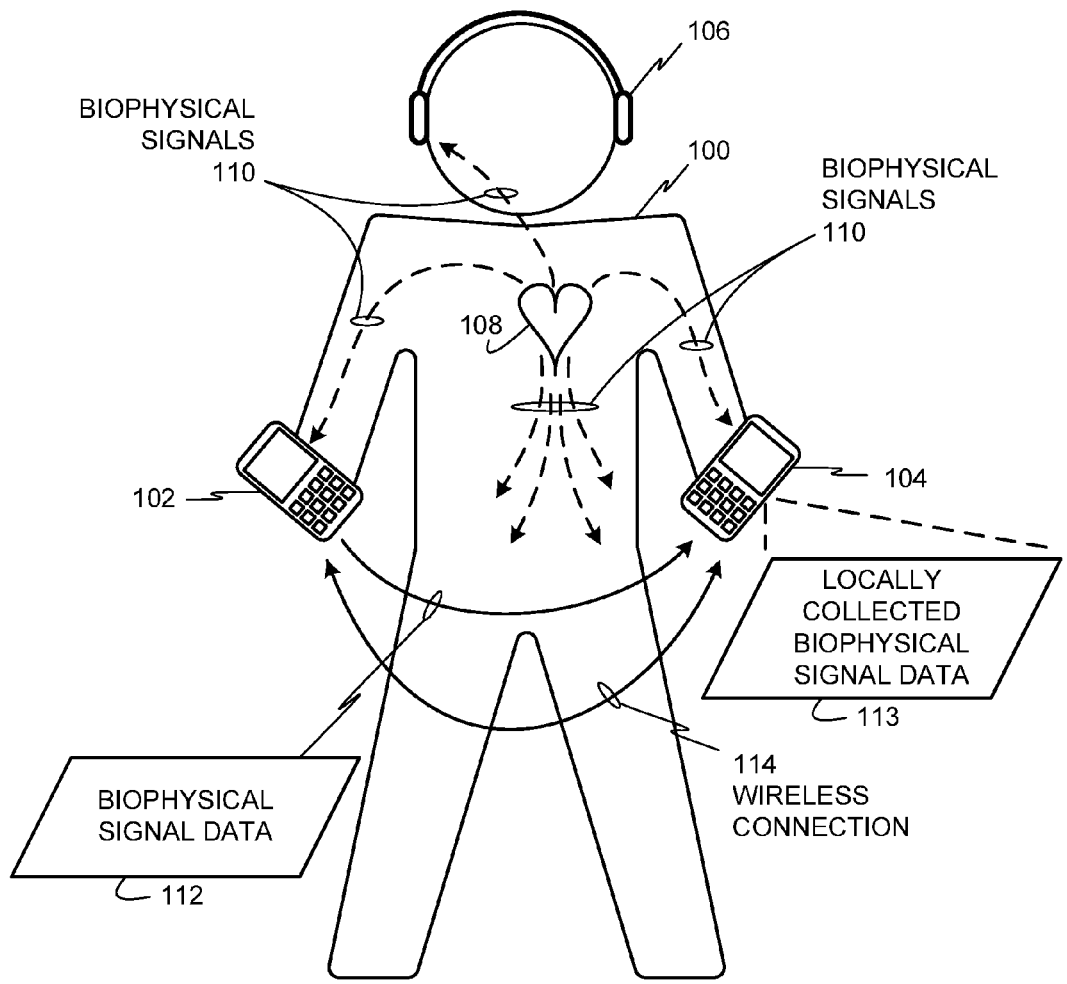
FIG. 1 depicts an example manner of using bio-certification processes to establish wireless connections between wireless-enabled devices.

Although the following discloses example methods, apparatus, and articles of manufacture including, among other components, software executed on hardware, it should be noted that such methods, apparatus, and articles of manufacture are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, apparatus, and articles of manufacture, persons having ordinary skill in the art will readily appreciate that the examples provided are not the only way to implement such methods, apparatus, and articles of manufacture.

It will be appreciated that for simplicity and clarity of illustration, where considered appropriate, reference numerals may be repeated among the figures to indicate corresponding or analogous elements. In addition, numerous specific details are set forth in order to provide a thorough understanding of example embodiments disclosed herein. However, it will be understood by those of ordinary skill in the art that example embodiments disclosed herein may be practiced without these specific details. In other instances, well-known methods, procedures and components have not been described in detail so as not to obscure example embodiments disclosed herein. Also, the description is not to be considered as limiting the scope of example embodiments disclosed herein.

Example methods, apparatus, and articles of manufacture are disclosed herein in connection with wireless-enabled devices, which may be any mobile communication device, mobile computing device, or any other element, entity, device, or service capable of communicating wirelessly. Mobile devices, also referred to as terminals, wireless terminals, mobile stations, communication stations, or user equipment (UE), may include mobile smart phones (e.g., BlackBerry® smart phones), wireless personal digital assistants (PDA), laptop/notebook/netbook computers with wireless adapters, etc. Example methods, apparatus, and articles of manufacture are disclosed herein in connection with Bluetooth® wireless communication technologies. However, such disclosed example methods, apparatus, and articles of manufacture may additionally or alternatively be implemented in connection with other wireless communication standards including the wireless local area network (WLAN) communication standard known as IEEE® 802.11, ZIGBEE® radio technology, wireless USB radio technology, and ultra-wideband (UWB) radio technology, or any other WLAN standards or personal area network (PAN) standards.

Example methods, apparatus, and articles of manufacture disclosed herein may be used to securely establish connections between devices based on bio-certification processes. Such example methods, apparatus, and articles of manufacture enable securely connecting two wireless-enabled devices by using biophysical signals generated by a person to confirm that both devices are in contact with the same person and, thus, within control of the same user. That is, known techniques require users to enter passwords and/or perform other user entry operations prior to making a successful connection to ensure that the connection is intended and that the user is aware of and consents to the connection being established. For example, synching or pairing of phones, smart phones, or other devices over wireless connections (e.g., Bluetooth® wireless connections) using known techniques involves a cumbersome user-driven process. User involvement in such known techniques for enabling Bluetooth® radios and/or other wireless technology radios to synch or connect mobile devices typically require users to activate a connecting/pairing process, initiate discovery of devices, and select discovered devices with which to connect. Such known connection processes burden users with a steep learning curve to understand how to properly navigate user interfaces and enter correct information (e.g., pass codes, device selections, etc.) to successfully establish device-to-device connections.

Unlike such known techniques that require much user involvement prior to making successful connections, example methods, apparatus, and articles of manufacture disclosed herein enable connections between devices based on those devices being in physical contact with the same person. That is, two devices in physical contact with the same person record and/or measure a biophysical signal of the person and compare collected biophysical signal data to confirm that the devices are actually in contact with the same person (e.g., being held by or worn by the same person). After both devices confirm that they have detected and/or measured the same biophysical signal, the devices can establish a connection between one another to transfer information therebetween (e.g., transfer files, exchange messages, stream audio and/or video, share an internet connection, etc.).

Example techniques disclosed herein enable users to use an intuitive, one-step or minimal-step process to establish device-to-device connections while allowing users to maintain control of specifying devices with which connections are permitted and when such connections are permitted. Example techniques disclosed herein also enable devices to be available at all times for establishing a connection in a secure manner. In this manner, operations such as synchronizing, exchanging, transferring, and/or streaming data can be automated without requiring users to perform a cumbersome manually-driven process to establish connections. Comparing collected biophysical signal data to confirm that connections can be made is referred to herein as bio-certification. Such bio-certification enables certifying that the same user is in control of two or more devices seeking to establish a connection(s) between one another.

FIG. 1 depicts an example manner of using example bio-certification processes to establish wireless connections between wireless-enabled devices. In the illustrated example, a person 100 holds example wireless-enabled mobile devices 102 and 104 and wears example wireless-enabled headphones 106. As discussed in detail below, the example wireless-enabled devices 102, 104, and 106 are configured to use example bio-certification processes disclosed herein to establish wireless connections between one another.

In the illustrated example of FIG. 1, bio-certification processes use a heart rate generated by a beating heart 108 of the person 100. As the heart 108 pumps blood through the body of the person 100, biophysical signals 110 in the form of a heart pulse are generated by and travel through the body of the person 100. Such biophysical signals 110 can be detected and/or measured using sensors (e.g., biophysical signal sensors, biometric sensors, etc.). In the illustrated example of FIG. 1, each of the wireless-enabled devices 102, 104, and 106 is provided with a respective sensor to detect the biophysical signals 110 and collect/store biophysical signal data based on those biophysical signals 110. The wireless-enabled devices 102, 104, and 106 can then exchange the collected biophysical signal data and perform comparisons between received biophysical signal data and their locally collected biophysical signal data to determine whether such data matches to enable establishing wireless connections between one another.

As shown in the illustrated example of FIG. 1, the wireless-enabled device 102 can detect the biophysical signals 110 of the person 100 and collect biophysical signal data 112 to initiate a bio-certification process to establish a wireless connection 114 with the wireless-enabled device 104. In the illustrated example, the biophysical signal data 112 is a heart rate or heart frequency calculated by the wireless-enabled device 102. Additionally or alternatively, the biophysical signal data 112 may be a heartbeat wavelength or some other pattern(s) or number(s) calculated based on the pumping action of the heart 108. In some examples, the biophysical signal data 112 may be related to, based on, or otherwise indicative of other characteristics of the person 110 such as blood pressure, body temperature, etc.

To request the wireless connection 114, the wireless-enabled device 102 broadcasts or otherwise sends the biophysical signal data 112 to the wireless-enabled device 104 via a broadcast channel or any other suitable communication channel (e.g., an open communication channel) prior to establishing the wireless connection 114. When the wireless-enabled device 104 receives the biophysical signal data 112, it compares the biophysical signal data 112 to locally collected biophysical signal data 113 collected by the wireless-enabled device 104 based on its operations of detecting the biophysical signals 110. When the wireless-enabled device 104 confirms that the biophysical signal data 112 matches (or substantially matches within a difference threshold range defined by, for example, a matching score range or threshold) its locally collected biophysical signal data 113, the wireless-enabled device 104 can accept the request from the wireless-enabled device 102 to establish the wireless connection 114. A similar process can be used to establish a wireless connection between one or both of the wireless-enabled devices 102 and/or 104 and the wireless-enabled headphones 106. For example, the wireless-enabled headphones 106 may be provided with sensors to detect the biophysical signals 110 at an ear region of the person 100. In some examples, to establish wireless connections, the wireless-enabled devices 102, 104, and 106 send their respective biophysical signal data (e.g., the biophysical signal data 112 and 113) to a central location (e.g., another device or a server). The biophysical signal data can then be compared at the central location (rather than at the wireless-enabled devices that collected the biophysical signal data) to confirm whether a match (or substantial match) is found. Comparison results or any other indications of whether a wireless connection can be established can then be communicated back to the wireless-enabled devices.

In the illustrated example, one or more of the wireless-enabled devices 102, 104, and 106 can initiate a request to establish a wireless connection (e.g., the wireless connection 114) based on a user-input (e.g., a user depressing a hardware button on a respective device or a soft icon displayed by a respective device) or based on a user (e.g., the person 100) coming into physical contact therewith. For example, any of the wireless-enabled devices 102, 104, and 106 may automatically begin a bio-certification process in response to detecting a biophysical signal 110 of the person 100 (e.g., when the person 100 picks up or puts on the wireless-enabled device). In some examples, the wireless-enabled devices 102, 104, and 106 may be configurable to initiate bio-certification processes based on automatic detection of biophysical signals 110 or based on user-input(s) requesting to initiate the bio-certification processes.

In the illustrated example, the wireless connection 114 remains established until the person 110 releases one or both of the wireless-enabled devices 102 and 104. In some examples, the wireless connection 114 may remain established until a requested data transfer (e.g., a file transfer) or media stream is finished. In such examples, the wireless connection 114 may be re-established via a bio-certification process each time a new data transfer (e.g., a file transfer) or media stream is requested.

In the illustrated example, the wireless-enabled devices 102 and 104 may establish the wireless connection 114 using Bluetooth® wireless technology, Institute of Electrical and Electronics Engineers (IEEE®) 802.11 wireless technology, or any other wireless technology suitable for connecting devices. In addition, although the example of FIG. 1 shows the wireless-enabled device 102 connecting to the wireless-enabled device 104, example techniques disclosed herein may also be used to establish wireless connections between any one or more of the wireless-enabled device 102, the wireless-enabled device 104, and/or the wireless-enabled headphones 106 and any other device not shown. Such other wireless-enabled devices may be tablet computing devices (e.g., the Research In Motion® BlackBerry® PlayBook™ tablet), personal computers, printers, projectors, or any other wireless-enabled device. Any such wireless-enabled device may be provided with a sensor to contact or engage a person (e.g., the person 100) for detecting a biophysical signal (e.g., the biophysical signals 110) of the person for use in establishing wireless connections (e.g., the wireless connection 114) with other devices as disclosed herein. Sensors for detecting biophysical signals may be integrally formed with a housing of a wireless-enabled device or may be attachable as a peripheral to a wireless-enabled device. For example, a desktop or laptop personal computer may have a sensor connected thereto via a universal serial bus (USB) connection or other wired or wireless connection.

In the illustrated example, the wireless-enabled devices 102, 104, and 106 beneficially use instant or currently measured biophysical signal data (e.g., the biophysical signal data 112) to enable establishing wireless connections (e.g., the wireless connection 114) instead of using previously measured and stored biophysical signal data. Configuring the wireless-enabled devices 102, 104, and 106 to use instant or currently measured biophysical signal data to compare to received biophysical signal data (e.g., the biophysical signal data 112) measured at and received from other devices increases the likelihood that two wireless-enabled devices held by or in contact with the same person (e.g., the person 100) will produce biophysical signal data resulting in an exact or near-exact match. For example, for instances in which the biophysical signal data 112 is based on heart-related signals (e.g., electrocardiogram (EKG) signals, heart rate, etc.) of the person 100, comparing current heart-related signal data with previously measured and stored heart-related signal data is more likely to produce non-matching results because a person's heart rate can fluctuate significantly over time. Thus, although not necessary, the example wireless-enabled device 102 of the illustrated example of FIG. 1 measures and collects instant or current biophysical signal data (e.g., the biophysical signal data 112) of the person 100 and sends the same to the wireless-enabled device 104. The wireless-enabled device 104 also measures and collects instant or current biophysical signal data of the person 100 and compares the locally collected biophysical signal data 113 with the received biophysical signal data 112 to determine whether the same person 100 is holding (and, thus, in control of) both of the wireless-enabled devices 102 and 104.

In some examples, wireless-enabled devices (e.g., the wireless-enabled devices 104 and/or 106) receiving a request to establish a wireless connection (e.g., the wireless connection 114) may compare received biophysical signal data (e.g., the biophysical signal data 112) with locally stored historical biophysical signal data rather than instantaneous or currently collected biophysical signal data such as the locally collected biophysical signal data 113. In such some examples, the historical biophysical signal data may be stored in association with location and time tags indicating a location at which a wireless-enabled device (e.g., the wireless-enabled device 104 or 106) was located when the historical biophysical signal data was collected and a time of day when the data was collected. In this manner, the wireless-enabled device may store multiple sets of historical biophysical signal data, each tagged with corresponding location and time tags. When another wireless-enabled device (e.g., the wireless-enabled device 102) sends a request for connection it sends current biophysical signal data (e.g., the biophysical signal data 112) reflective of a person's current heart rate along with location and time tags indicating a current location of the wireless-enabled device and a current time of day. In this manner, a wireless-enabled device (e.g., the wireless-enabled device 104 or 106) receiving the request for connection and the current biophysical signal data can use the received location and time tags to retrieve stored historical biophysical signal data having the same (or substantially the same within an acceptable tolerance or threshold) location and time tags. By retrieving historical biophysical signal data associated with the same location and time tags, there is a greater likelihood that the retrieved historical biophysical signal data will match (or substantially match) the current biophysical signal data received from the wireless-enabled device requesting a connection so long as the current biophysical signal data is collected from the same person from which the historical biophysical signal data was collected. That is, the person's heart rate will likely be influenced by the same environmental factors when the person is located at the same location (e.g., work, home, a gym, a shopping center, a coffee shop, a retail establishment, etc.) at the same time of day. Thus, the person's heart rate on any given day at a particular location at a particular time of day will be expected to vary by only some small amount, if at all, from that same person's heart rate on any prior day at the same location and time when historical biophysical signal data was collected. In some examples, multiple sets of historical biophysical signal data collected on different days could be averaged (or processed using some other mathematical/statistical operation) to form a standard or average historical biophysical signal data for a particular time and location. In such some examples, an acceptable variation can be determined based on the average variation between multiple, separate historical biophysical signal data for a particular time and location. The acceptable variation can then be used to form a tolerance or threshold matching score that indicates an acceptable substantial match between current biophysical signal data and historical biophysical signal data. If at any subsequent time a wireless connection cannot be established due to the current biophysical signal data varying from the historical biophysical signal data by more than the determined acceptable variation, one or both of the wireless-enabled devices sought to be wirelessly connected can be configured to display icons on a graphical user interface that are selectable by the user to suggest activities that would affect the user's current heart rate (or a heart waveform such as an EKG waveform) to match the historical biophysical signal data. In this manner, a person's current biophysical signal data can match (or sufficiently match) that same person's stored historical biophysical signal data to allow establishing a wireless connection between wireless-enabled devices.

Figure 2:
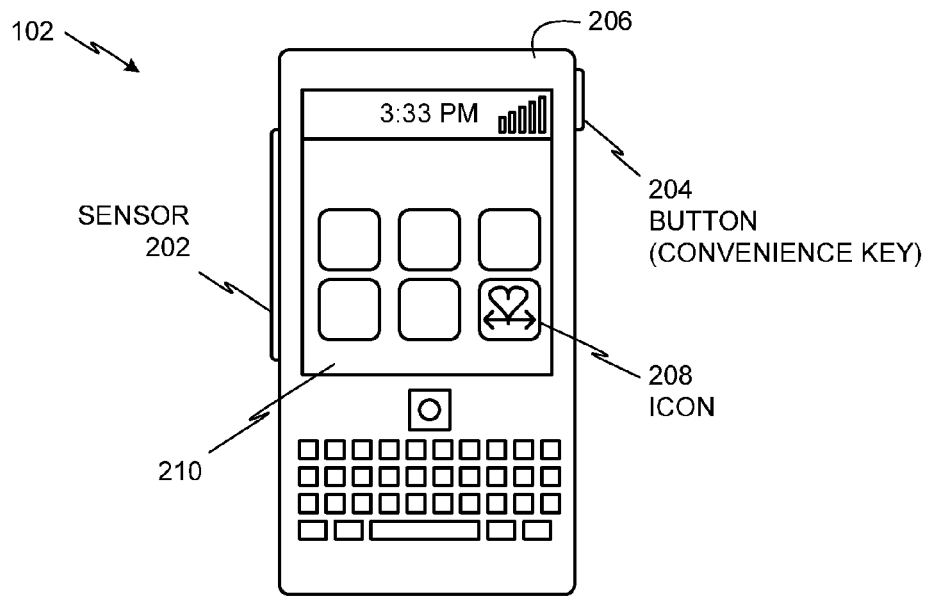
FIG. 2 depicts an example wireless-enabled device of FIG. 1 configured to establish wireless connections with other wireless-enabled devices based on a bio-certification process.

FIG. 2 depicts the example wireless-enabled device 102 of FIG. 1 configured to establish wireless connections (e.g., the wireless connection 114 of FIG. 1) with other wireless-enabled devices (e.g., one or both of the wireless-enabled devices 104 and 106 of FIG. 1) based on a bio-certification process as discussed above in connection with FIG. 1. In the illustrated example of FIG. 1, the wireless-enabled device 102 is depicted as a smart phone. However, the structures and features disclosed in connection with FIG. 2 to enable performing bio-certification processes may be implemented in connection with other types of wireless-enabled devices.

As shown in FIG. 2, the wireless-enabled device 102 is provided with a sensor 202 to detect the biophysical signals 110 of the person 100 shown in FIG. 1. In the illustrated example, the sensor 202 is configured to contact or engage one or more fingers of the person 100 and/or the palm of a hand of the person 100 when the person 100 holds the wireless-enabled device 102. Such surface contact with the person 100 facilitates detecting and measuring the biophysical signals 110 via the sensor 202. The example sensor 202 of FIG. 2 is connected to one or more circuits in the wireless-enabled device 102 that enable the wireless-enabled device 102 to measure the biophysical signals 110 and collect the biophysical signal data 112 (FIG. 1) based on the biophysical signals 110. In some examples, the wireless-enabled device 102 may be configured to automatically detect the biophysical signals 110 and automatically begin a bio-certification process in response to a user grabbing, holding, or wearing the wireless-enabled device 102 or otherwise physically contacting the sensor 202.

Although the sensor 202 is shown as protruding from the wireless-enabled device 102, in other examples, the sensor 202 may be flat, seamless, and/or unitarily formed with the housing 206. In some examples, the sensor 202 may be a substantially large portion of a surface area of the housing 206 to enable contacting a relatively larger surface area of the person 100. In some examples, the wireless-enabled device 102 may be provided with multiple sensors substantially similar or identical to the sensor 202 to facilitate measuring and collecting biophysical signal data 112 based on various techniques employed by the person 100 or any other person for holding or wearing the wireless-enabled device 102. Sensors substantially similar to the sensor 202 of FIG. 2 may be adapted for use in connection with wireless-enabled devices that are wearable such as the wireless-enabled headphones 106 of FIG. 1. For example, sensors for wearable wireless-enabled devices may be structured and located on the devices in configurations that facilitate contact with body parts or body locations of users at which biophysical signals (e.g., the biophysical signals 110 of FIG. 1) can be detected.

Also shown in FIG. 2, the wireless-enabled device 102 is provided with a hardware button 204 (e.g., a convenience key that is user-programmable to start a particular process or application) located on and/or protruding from a housing 206 of the wireless-enabled device 102. The wireless-enabled device 102 is also shown displaying an icon 208 on a display 210 of the wireless-enabled device 102. In the illustrated example of FIG. 2, the hardware button 204 and the icon 208 are configured to receive user inputs to initiate bio-certification processes to establish wireless connections (e.g., the wireless connection 114 of FIG. 1) as described above in connection with FIG. 1. For example, when in physical contact with the sensor 202, the person 100 (FIG. 1) may depress the button 204 or select the icon 208 to initiate a bio-certification process during which the wireless-enabled device 102 measures and collects the biophysical signal data 112 via the sensor 202 based on the biophysical signals 110 of FIG. 1. In some examples, the wireless-enabled device 102 may be provided with only one of the button 204 or the icon 208 to initiate bio-certification processes.

Figure 3:
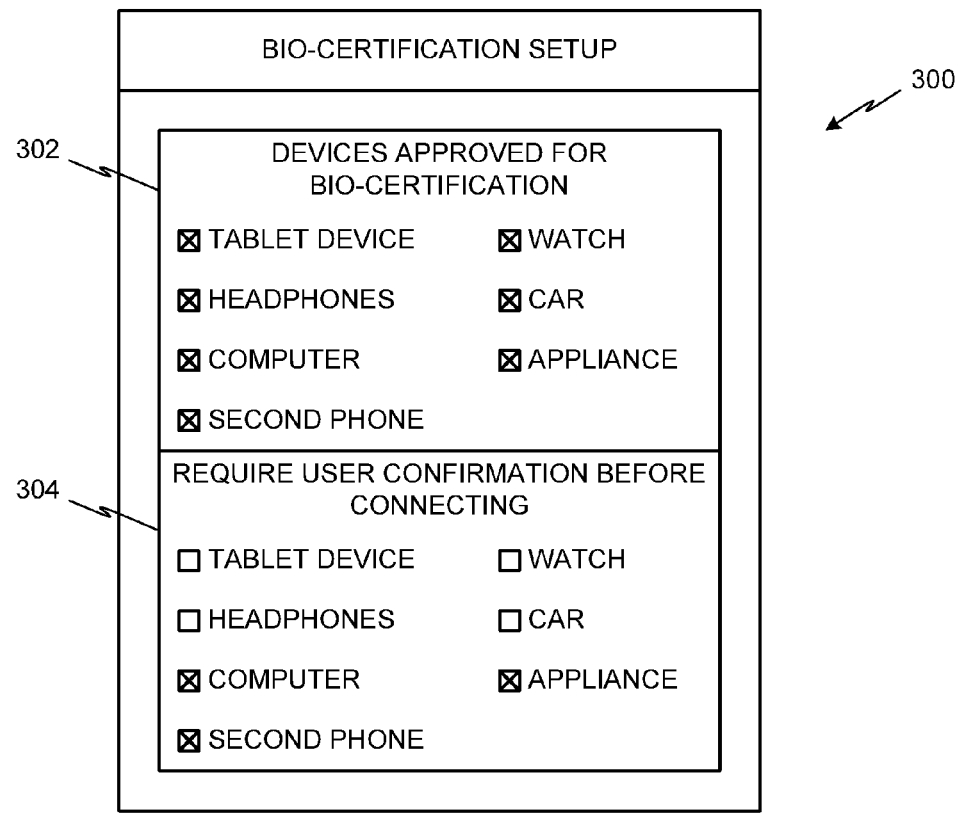
FIG. 3 depicts an example graphical user interface for use with the example wireless-enabled device of FIGS. 1 and 2 to setup the wireless-enabled device for using a bio-certification process to establish wireless connections with other wireless-enabled devices.

FIG. 3 depicts an example bio-certification setup graphical user interface (GUI) 300 for use with the example wireless-enabled device 102 of FIGS. 1 and 2 to setup the wireless-enabled device 102 for using a bio-certification process to establish wireless connections (e.g., the wireless connection 114 of FIG. 1) with other wireless-enabled devices (e.g., the wireless-enabled devices 104 and 106 of FIG. 1). In the illustrated example, the bio-certification setup GUI 300 is provided with an approved-devices setup display area 302 and a user-confirmation setup display area 304. In the illustrated example, the approved-devices setup display area 302 enables users to specify devices with which the wireless-enabled device 102 may establish wireless connections (e.g., the wireless connection 114 of FIG. 1) using bio-certification processes. In the example of FIG. 3, a user has specified that the wireless-enabled device 102 may use bio-certification processes to establish wireless connections with a tablet device, headphones, a computer, a second phone, a watch, a car, an appliance. In other examples, fewer of the devices listed in FIG. 3 may be selected or approved by a user.

In the illustrated example, the user-confirmation setup display area 304 enables users to specify devices that require user-confirmation before successfully establishing wireless connections (e.g., the wireless connection 114 of FIG. 1) between the wireless-enabled device 102 and such devices specified in the user-confirmation setup display area 304. In the illustrated example of FIG. 3, a user has specified that user-confirmation is required before establishing a wireless connection with a 'computer,' a 'second phone,' and an 'appliance,' while user-confirmation is not required for a 'tablet device,' 'headphones,' a 'watch,' or a 'car.'

According to the user-specified setup shown in the user-confirmation setup display area 304, a bio-certification process between the wireless-enabled device 102 and the computer may be initiated, but will result in successfully establishing a wireless connection only if matching (or substantially matching) biophysical signal data is found and if a user confirms that the wireless connection may be established. For devices not requiring user-confirmation based on the user-confirmation setup display area 304 of FIG. 3, such devices can establish a wireless connection setup with the wireless-enabled device 102 without user confirmation. Thus, a bio-certification process between the wireless-enabled device 102 and the 'tablet device' listed in the user-confirmation setup display area 304 will result in successfully establishing a wireless connection if matching (or substantially matching) biophysical signal data is found without needing to receive user confirmation that the wireless connection may be established.

While the devices listed in FIG. 3 are indicated by generic device type names, in other examples the devices listed in FIG. 3 may be indicated by more specific identifiers (e.g., identifiers to uniquely identify particular devices discovered by the wireless-enabled device 102). For example, instead of 'tablet device', a unique identifier may be 'Joe's BlackBerry® PlayBook™' and instead of 'appliance', a unique identifier may be 'family room television' or 'Acme-brand television.'

Figure 4:
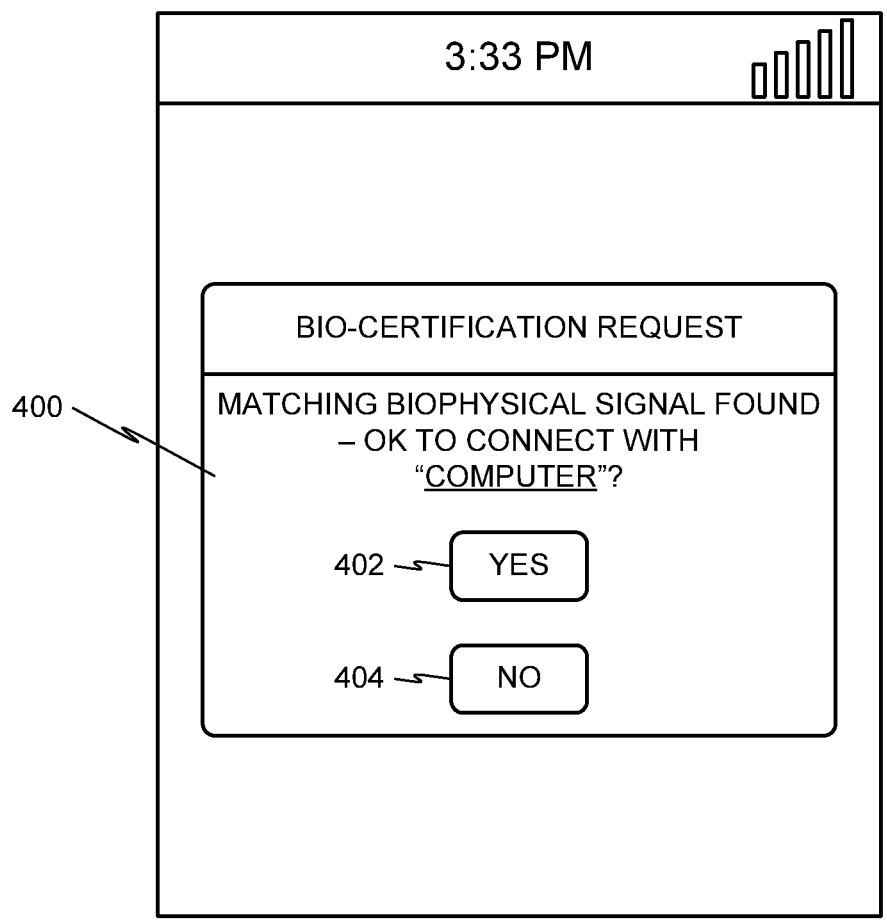
FIG. 4 depicts an example graphical user interface for displaying a message via the example wireless-enabled device of FIGS. 1 and 2 requesting user-confirmation to establish a wireless connection with another wireless-enabled device.

FIG. 4 depicts an example GUI message 400 to be displayed via the example wireless-enabled device 102 of FIGS. 1 and 2 (or any other wireless-enabled device) requesting user-confirmation to establish a wireless connection with another wireless-enabled device (e.g., the wireless-enabled device 104 or the wireless-enabled headphones 106 of FIG. 1). In the illustrated example of FIG. 4, the GUI message 400 requests a user to confirm whether the wireless-enabled device can proceed with establishing a wireless connection (e.g., the wireless connection 114 of FIG. 1) with a computer. In some examples, the wireless-enabled device 102 displays the GUI message 400 of the illustrated example (or a similar GUI message) in response to receiving an acknowledgement from the discovered wireless-enabled device that biophysical signal data collected at the discovered wireless-enabled device matches (or substantially matches) biophysical signal data (e.g., the biophysical signal data 112 of FIG. 1) collected at the wireless-enabled device 102. If a user (e.g., the person 100 of FIG. 1) selects a 'YES' option 402 of the GUI message 400, the wireless-enabled device 102 and the discovered wireless-enabled device establish a wireless connection therebetween (provided matching (or substantially matching) biophysical signal data is found between the two wireless-enabled devices). If the user selects a 'NO' option 404 of the GUI message 400, a wireless connection is not established between the wireless-enabled device 102 and the discovered wireless-enabled device.

Figure 5:
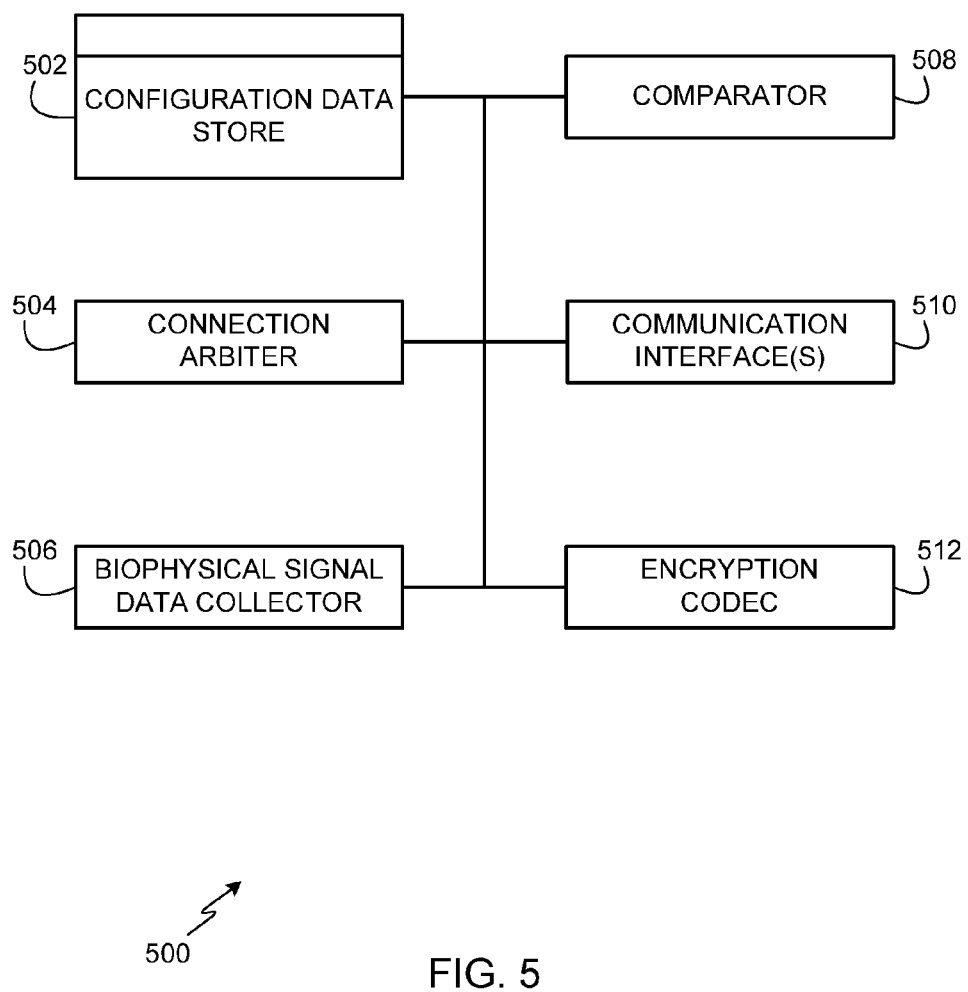
FIG. 5 depicts an example apparatus to enable the example wireless-enabled device of FIGS. 1 and 2 to establish wireless connections based on bio-certification processes.

FIG. 5 depicts an example apparatus 500 to enable the example wireless-enabled device 102 (and/or the wireless-enabled devices 104 and/or 106) of FIGS. 1 and 2 to establish wireless connections (e.g., the wireless connection 114 of FIG. 1) based on bio-certification processes. In some examples, the apparatus 500 of the illustrated example may be implemented using the example processor system described below in connection with FIG. 6. In the illustrated example of FIG. 5, the apparatus 500 is provided with a configuration data store 502, a connection arbiter 504, a biophysical signal data collector 506, a comparator 508, one or more communication interface(s) 510, and an encryption codec 512. The configuration data store 502, the connection arbiter 504, the biophysical signal data collector 506, the comparator 508, the communication interface(s) 510, and/or the encryption codecs 512 may be implemented using any desired combination of hardware, firmware, and/or software. For example, one or more integrated circuits, discrete semiconductor components, and/or passive electronic components may be used. Thus, for example, the configuration data store 502, the connection arbiter 504, the biophysical signal data collector 506, the comparator 508, the communication interface(s) 510, and/or the encryption codec 512 or parts thereof, could be implemented using one or more circuit(s), programmable processor(s), application specific integrated circuit(s) (ASIC(s)), programmable logic device(s) (PLD(s)), field programmable logic device(s) (FPLD(s)), etc. The configuration data store 502, the connection arbiter 504, the biophysical signal data collector 506, the comparator 508, the communication interface(s) 510, and/or the encryption codec 512 or parts thereof, may be implemented using instructions, code, and/or other software and/or firmware, etc. stored on a machine accessible medium and executable by, for example, a processor (e.g., the main processor 602 of FIG. 6). When any of the appended claims are read to cover a purely software implementation, at least one of the configuration data store 502, the connection arbiter 504, the biophysical signal data collector 506, the comparator 508, the communication interface(s) 510, or the encryption codec 512 is hereby expressly defined to include a tangible medium such as a solid state memory, a magnetic memory, a DVD, a CD, etc.

Turning in detail to FIG. 5, the apparatus 500 is provided with the configuration data store 502 to store user-specified preferences associated with using bio-certification processes to connect with other wireless-enabled devices. In the illustrated example, the configuration data store 502 stores preferences specified by a user via the bio-certification setup GUI 300 of FIG. 3. Additionally or alternatively, the configuration data store 502 may store preferences specified by a user through means other than the bio-certification setup GUI 300. Such other means include one or more of, for example, other GUIs displayable by the wireless-enabled device 102, a computer capable of communicating with the wireless-enabled device 102, a web page, or any other suitable device and/or interface.

To determine whether wireless connections (e.g., the wireless connection 114 of FIG. 1) are allowable and/or can be established, the apparatus 500 of the illustrated example is provided with the connection arbiter 504. In the illustrated example, the connection arbiter 504 accesses the configuration data store 502 to determine which devices (e.g., devices listed in the bio-certification setup GUI 300) a user has specified as approved for bio-certification and which devices the user has approved for automatically establishing wireless connections without requiring user confirmation. During a bio-certification process, the wireless-enabled device 102 performs a discovery process to find other wireless-enabled devices within communication proximity. When the wireless-enabled device 102 receives identities of nearby discovered devices, the connection arbiter 504 compares the discovered devices with devices approved for bio-certification in the configuration data store 502.

The connection arbiter 504 also analyzes comparison results of locally collected biophysical signal data (e.g., the locally collected biophysical signal data 113 of FIG. 1) with biophysical signal data (e.g., the biophysical signal data 112 of FIG. 1) received from another wireless-enabled device. In this manner, if the connection arbiter 504 determines that the two sets of data match or substantially match, the connection arbiter 504 allows the bio-certification process to proceed. In the illustrated example, a substantial match occurs when two biophysical signal data sets match within an acceptable tolerance or threshold based on a matching score associated with the compared biophysical signal data. In the illustrated example, the connection arbiter 504 stores or can access a stored matching score threshold indicative of a worst-case inexact match for which the connection arbiter 504 can approve establishing a wireless connection. In some examples, one or more matching score threshold(s) can be defined by a user, a device manufacturer, or a telecommunication system network operator to indicate worst-case inexact matches for which the connection arbiter 504 can allow establishing of wireless connections. In some examples, matching score thresholds are stored in the configuration data store 502. In addition, respective matching score thresholds may be specified for different devices (e.g., the devices listed in the bio-certification setup GUI 300 of FIG. 3).

In addition, while performing a bio-certification process with an approved device and prior to successfully establishing a wireless connection, the connection arbiter 504 checks the configuration data store 502 to determine whether user-confirmation is required for the particular approved device before establishing the wireless connection. If user-confirmation is required, the connection arbiter 504 does not allow or permit establishing of the wireless connection until it has received user confirmation to allow the wireless connection. Such user confirmation may be solicited and received via the GUI message 400 of FIG. 4.

To collect biophysical signal data (e.g., the biophysical signal data 112 of FIG. 1), the apparatus 500 of the illustrated example is provided with the biophysical signal data collector 506. In the illustrated example, the biophysical signal data collector 506 is in communication with a sensor (e.g., the sensor 202) configured to engage or contact a person (e.g., the person 100 of FIG. 1) at a location on the person's body that provides access to detecting biophysical signals (e.g., the biophysical signals 110 of FIG. 1) of the person. The biophysical signal data collector 506 of the illustrated example receives signals (e.g., electrical signals) from the sensor 202 representative of the biophysical signals 110, translates or converts the signals into a digital format, and measures the digital signals to collect biophysical signal data (e.g., the biophysical signal data 112 of FIG. 1). In the illustrated example, the biophysical signal data collector 506 analyzes the digital signals to determine a heart pulse rate or frequency. The biophysical signal data collector 506 then uses the heart pulse rate or frequency as the biophysical signal data 112. In some examples, the biophysical signal data collector 506 may collect heart beat waveforms (e.g., EKG waveforms) and use such waveforms as the biophysical signal data 112. In yet other examples, the biophysical signal data collector 506 may determine, form, or generate any other type of data (e.g., amplitudes of maximum or minimum heart beat pulses, quantity of maximum or minimum heart beat pulses above/below a threshold, encrypted or hash or random values using heart rates as seed values or keys or base values, etc.) based on the digital form of the detected biophysical signals 110 to generate the biophysical signal data 112 for purposes of performing comparisons during bio-certification processes.

To compare locally collected biophysical signal data (e.g., the locally collected biophysical signal data 113 of FIG. 1) to biophysical signal data (e.g., the biophysical signal data 112 of FIG. 1) received from other wireless-enabled devices, the apparatus 500 of the illustrated example is provided with a comparator 508. In the illustrated example, the comparator 508 is configured to compare heart pulse rate or frequency data. Additionally or alternatively, the comparator 508 may be configured to compare any other type of data that is represented in biophysical signal data (e.g., the biophysical signal data 112) and may involve comparisons of values and/or comparisons of patterns or waveforms. Such other data may be, for example, heart beat waveforms (e.g., EKG waveforms), amplitudes of maximum or minimum heart beat pulses, quantity of maximum or minimum heart beat pulses above/below a threshold, encrypted or random values using heart rates as seed or base values, etc.

In the illustrated example of FIG. 5, the comparator 508 determines a matching score indicative of how comparatively close two compared data are to one another. For example, the comparator 508 of the illustrated example generates a match score of one (1) for an exact match between two compared biophysical signal data and produces match scores of less than one (1) for inexact matches. In the illustrated example, the comparator 508 sends match scores to the connection arbiter 504, and the connection arbiter 504 compares the match scores to a match score threshold indicative of a worst-case inexact match for which the connection arbiter 504 can approve establishing a wireless connection.

In the illustrated example, the apparatus 500 is provided with one or more communication interface(s) 510 via which wireless connections (e.g., the wireless connection 114 of FIG. 1) are established. In the illustrated example, the communication interface(s) 510 are wireless. Example wireless communication technologies that may be employed to implement the one or more communication subsystem(s) 1012 include, for example, IEEE® 802.11 radio technology, BLUETOOTH® radio technology, ZIGBEE® radio technology, wireless USB radio technology, and ultra-wideband (UWB) radio technology. Although example methods, apparatus, and articles of manufacture are disclosed herein in connection with establishing wireless connections, such as the wireless connection 114, between devices, such example methods, apparatus, and articles of manufacture disclosed herein may be similarly used to establish wired connections between devices based on bio-certification processes. In such examples, the communication interface(s) 510 may include one or more wired communication interfaces.

In some examples, the apparatus 500 is provided with the encryption codec 512 to generate, encipher or code hash values based on biophysical signal data (e.g., the biophysical signal data 112 of FIG. 1) to send to other wireless-enabled devices for establishing wireless connections based on bio-certification. The encryption codec 512 also enables the apparatus 500 to decode or decipher hash values received from other wireless-enabled devices based on locally collected biophysical signal data (e.g., the locally collected biophysical signal data 113 of FIG. 1). In such examples, the encryption codec 512 at the wireless-enabled device 102 of FIG. 1 uses the biophysical signal data 112 collected at the wireless-enabled device 102 as a private key to generate a hash of public or shared information (e.g., a value or information that is known to all wireless-enabled devices). The wireless-enabled device 102 then broadcasts the hash to all wireless-enabled devices in communication range. The wireless-enabled device 104 receives the broadcast hash and uses its encryption codec (which is substantially similar or identical to the encryption codec 512 of FIG. 5) to decode or decipher the received hash using the locally collected biophysical signal data 113 of FIG. 1 as the private key. If the biophysical signal data 112 and the locally collected biophysical signal data 113 corresponding to the same person as shown in FIG. 1, the private key used to decode the hash at the wireless-enabled device 104 is the same or substantially the same as the private key used to encode the hash at the wireless-enabled device 102. Thus, when the wireless-enabled device 104 decodes the hash, it will recover the same public or shared information. The wireless-enabled device 104 can then use its comparator (which is substantially the same or identical to the comparator 508) to compare the recovered information to its locally stored public or shared information to confirm a match. A confirmed match informs a connection arbiter 504 of the wireless-enabled device 104 that a wireless connection (e.g., the wireless connection 114 of FIG. 1) is allowed or permissible.

Figure 6:
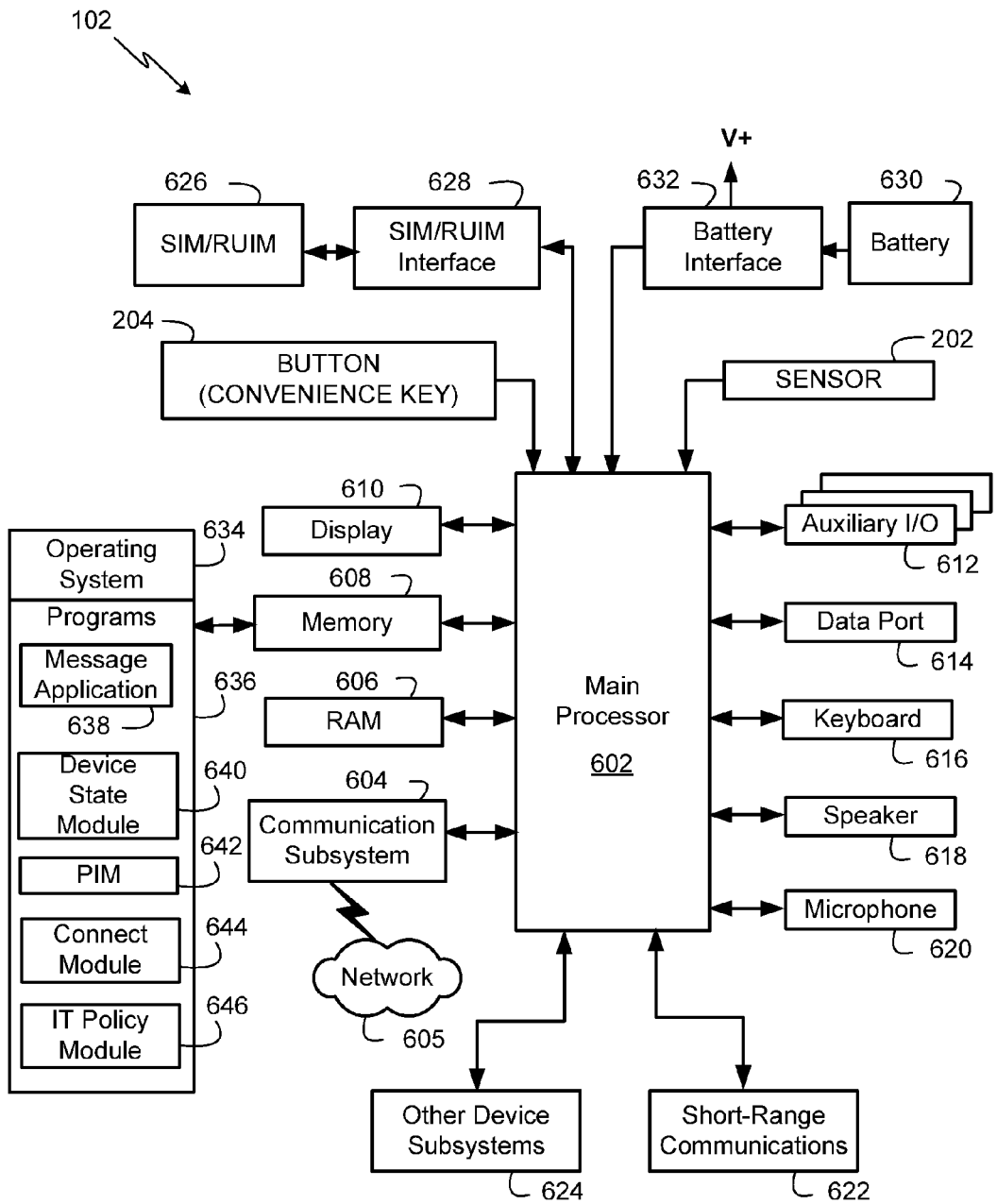
FIG. 6 depicts an example block diagram of the wireless-enabled device of FIGS. 1 and 2.

FIG. 6 depicts a block diagram of an example implementation of a processor system that may be used to implement the wireless-enabled device 102. Although the processor system of FIG. 6 is described as implementing the wireless-enabled device 102, a processor system identical or similar to the processor system depicted in FIG. 6 may be used to implement the wireless-enabled device 104 of FIG. 1, the wireless-enabled headphones 106 of FIG. 1, and/or the apparatus 500 of FIG. 5. In the illustrated example, the wireless-enabled device 102 is a two-way communication device with advanced data communication capabilities including the capability to communicate with other wireless-enabled devices or computer systems through a network of transceiver stations. The wireless-enabled device 102 may also have the capability to allow voice communication. Depending on the functionality provided by the wireless-enabled device 102, it may be referred to as a data messaging device, a two-way pager, a cellular telephone with data messaging capabilities, a smart phone, a wireless Internet appliance, or a data communication device (with or without telephony capabilities). To aid the reader in understanding the structure of the wireless-enabled device 102 and how it communicates with other devices and host systems, FIG. 6 will now be described in detail.

Referring to FIG. 6, the wireless-enabled device 102 includes a number of components such as a main processor 602 that controls the overall operation of the wireless-enabled device 102. In the illustrated example, the sensor 202 and the button (convenience key) 204 described above in connection with FIG. 2 are connected to the main processor 602. Communication functions, including data and voice communications, are performed through a communication subsystem 604. The communication subsystem 604 receives messages from and sends messages to a wireless network 605. In the illustrated example of the wireless-enabled device 102, the communication subsystem 604 is configured in accordance with the Global System for Mobile Communication (GSM) and General Packet Radio Services (GPRS) standards. The GSM/GPRS wireless network is used worldwide and it is expected that these standards will be superseded eventually by Enhanced Data GSM Environment (EDGE) and Universal Mobile Telecommunications Service (UMTS). New standards are still being defined, but it is believed that they will have similarities to the network behavior described herein, and it will also be understood by persons skilled in the art that the example implementations described herein are intended to use any other suitable standards that are developed in the future. The wireless link connecting the communication subsystem 604 with the wireless network 605 represents one or more different Radio Frequency (RF) channels, operating according to defined protocols specified for GSM/GPRS communications. With newer network protocols, these channels are capable of supporting both circuit switched voice communications and packet switched data communications.

Although the wireless network 605 associated with the wireless-enabled device 102 is a GSM/GPRS wireless network in one exemplary implementation, other wireless networks may also be associated with the wireless-enabled device 102 in variant implementations. The different types of wireless networks that may be employed include, for example, data-centric wireless networks, voice-centric wireless networks, and dual-mode networks that can support both voice and data communications over the same physical base stations. Combined dual-mode networks include, but are not limited to, Code Division Multiple Access (CDMA) or CDMA2000 networks, GSM/GPRS networks (as mentioned above), and future third-generation (3G) networks like EDGE and UMTS. Some other examples of data-centric networks include WiFi 802.11, MOBITEX® and DATATAC® network communication systems. Examples of other voice-centric data networks include Personal Communication Systems (PCS) networks like GSM and Time Division Multiple Access (TDMA) systems.

The main processor 602 also interacts with additional subsystems such as a Random Access Memory (RAM) 1106, a persistent memory 608 (e.g., a non-volatile memory), a display 610, an auxiliary input/output (I/O) subsystem 612, a data port 614, a keyboard 616, a speaker 618, a microphone 620, short-range communications 622, and other device subsystems 624.

Some of the subsystems of the wireless-enabled device 102 perform communication-related functions, whereas other subsystems may provide "resident" or on-device functions. By way of example, the display 610 and the keyboard 616 may be used for both communication-related functions, such as entering a text message for transmission over the network 605, and device-resident functions such as a calculator or task list.

The wireless-enabled device 102 can send and receive communication signals over the wireless network 605 after required network registration or activation procedures have been completed. Network access is associated with a subscriber or user of the wireless-enabled device 102. To identify a subscriber, the wireless-enabled device 102 requires a SIM/RUIM card 626 (i.e. Subscriber Identity Module or a Removable User Identity Module) to be inserted into a SIM/RUIM interface 628 in order to communicate with a network. The SIM card or RUIM 626 is one type of a conventional "smart card" that can be used to identify a subscriber of the wireless-enabled device 102 and to personalize the wireless-enabled device 102, among other things. Without the SIM card 626, the wireless-enabled device 102 is not fully operational for communication with the wireless network 605. By inserting the SIM card/RUIM 626 into the SIM/RUIM interface 628, a subscriber can access all subscribed services. Services may include: web browsing and messaging such as e-mail, voice mail, Short Message Service (SMS), and Multimedia Messaging Services (MMS). More advanced services may include: point of sale, field service and sales force automation, bio-certification processes to establish wireless connections, such as the wireless connection 114 of FIG. 1. The SIM card/RUIM 626 includes a processor and memory for storing information. Once the SIM card/RUIM 626 is inserted into the SIM/RUIM interface 628, it is coupled to the main processor 602. In order to identify the subscriber, the SIM card/RUIM 626 can include some user parameters such as an International Mobile Subscriber Identity (IMSI). An advantage of using the SIM card/RUIM 626 is that a subscriber is not necessarily bound by any single physical mobile device. The SIM card/RUIM 626 may store additional subscriber information for a wireless-enabled device or mobile device as well, including datebook (or calendar) information and recent call information. Alternatively, user identification information can also be programmed into the persistent memory 608.

The wireless-enabled device 102 is a battery-powered device and includes a battery interface 632 for receiving one or more rechargeable batteries 630. In at least some embodiments, the battery 630 can be a smart battery with an embedded microprocessor. The battery interface 632 is coupled to a regulator (not shown), which assists the battery 630 in providing power V+ to the wireless-enabled device 102. Although current technology makes use of a battery, future technologies such as micro fuel cells may provide the power to the wireless-enabled device 102.

The wireless-enabled device 102 also includes an operating system 634 and software components 636 to 646 which are described in more detail below. The operating system 634 and the software components 636 to 646 that are executed by the main processor 602 are typically stored in a persistent store such as the persistent memory 608, which may alternatively be a read-only memory (ROM) or similar storage element (not shown). Those skilled in the art will appreciate that portions of the operating system 634 and the software components 636 to 646, such as specific device applications, or parts thereof, may be temporarily loaded into a volatile store such as the RAM 606. Other software components can also be included, as is well known to those skilled in the art.

The subset of software applications 636 that control basic device operations, including data and voice communication applications, will normally be installed on the wireless-enabled device 102 during its manufacture. Other software applications include a message application 638 that can be any suitable software program that allows a user of the wireless-enabled device 102 to send and receive electronic messages. Various alternatives exist for the message application 638 as is well known to those skilled in the art. Messages that have been sent or received by the user are typically stored in the persistent memory 608 of the wireless-enabled device 102 or some other suitable storage element in the wireless-enabled device 102. In at least some embodiments, some of the sent and received messages may be stored remotely from the wireless-enabled device 102 such as in a data store of an associated host system that the wireless-enabled device 102 communicates with.

The software applications can further include a device state module 640, a Personal Information Manager (PIM) 642, and other suitable modules (not shown). The device state module 640 provides persistence (i.e., the device state module 640 ensures that important device data is stored in persistent memory, such as the persistent memory 608, so that the data is not lost when the wireless-enabled device 102 is turned off or loses power).

The PIM 642 includes functionality for organizing and managing data items of interest to the user, such as, but not limited to, e-mail, contacts, calendar events, voice mails, appointments, and task items. A PIM application has the ability to send and receive data items via the wireless network 605. PIM data items may be seamlessly integrated, synchronized, and updated via the wireless network 605 with the mobile device subscriber's corresponding data items stored and/or associated with a host computer system. This functionality creates a mirrored host computer on the wireless-enabled device 102 with respect to such items. This can be particularly advantageous when the host computer system is the mobile device subscriber's office computer system.

The wireless-enabled device 102 also includes a connect module 644, and an IT policy module 646. The connect module 644 implements the communication protocols that are required for the wireless-enabled device 102 to communicate with the wireless infrastructure and any host system, such as an enterprise system, that the wireless-enabled device 102 is authorized to interface with.

The connect module 644 includes a set of APIs that can be integrated with the wireless-enabled device 102 to allow the wireless-enabled device 102 to use any number of services associated with the enterprise system. The connect module 644 allows the wireless-enabled device 102 to establish an end-to-end secure, authenticated communication pipe with the host system. A subset of applications for which access is provided by the connect module 644 can be used to pass IT policy commands from the host system (e.g., from an IT policy server of a host system) to the wireless-enabled device 102. This can be done in a wireless or wired manner. These instructions can then be passed to the IT policy module 646 to modify the configuration of the wireless-enabled device 102. Alternatively, in some cases, the IT policy update can also be done over a wired connection.

The IT policy module 646 receives IT policy data that encodes the IT policy. The IT policy module 646 then ensures that the IT policy data is authenticated by the wireless-enabled device 102. The IT policy data can then be stored in the flash memory 606 in its native form. After the IT policy data is stored, a global notification can be sent by the IT policy module 646 to all of the applications residing on the wireless-enabled device 102. Applications for which the IT policy may be applicable then respond by reading the IT policy data to look for IT policy rules that are applicable.

The IT policy module 646 can include a parser (not shown), which can be used by the applications to read the IT policy rules. In some cases, another module or application can provide the parser. Grouped IT policy rules, described in more detail below, are retrieved as byte streams, which are then sent (recursively, in a sense) into the parser to determine the values of each IT policy rule defined within the grouped IT policy rule. In at least some embodiments, the IT policy module 1146 can determine which applications (e.g., bio-certification processes to establish wireless communications based on comparisons of biophysical signal data, such as the biophysical signal data 112 of FIG. 1) are affected by the IT policy data and send a notification to only those applications. In either of these cases, for applications that aren't running at the time of the notification, the applications can call the parser or the IT policy module 646 when they are executed to determine if there are any relevant IT policy rules in the newly received IT policy data.

All applications that support rules in the IT Policy are coded to know the type of data to expect. For example, the value that is set for the "WEP User Name" IT policy rule is known to be a string; therefore the value in the IT policy data that corresponds to this rule is interpreted as a string. As another example, the setting for the "Set Maximum Password Attempts" IT policy rule is known to be an integer, and therefore the value in the IT policy data that corresponds to this rule is interpreted as such.

After the IT policy rules have been applied to the applicable applications or configuration files, the IT policy module 646 sends an acknowledgement back to the host system to indicate that the IT policy data was received and successfully applied.

Other types of software applications can also be installed on the wireless-enabled device 102. These software applications can be third party applications, which are added after the manufacture of the wireless-enabled device 102. Examples of third party applications include games, calculators, utilities, etc.

The additional applications can be loaded onto the wireless-enabled device 102 through at least one of the wireless network 605, the auxiliary I/O subsystem 612, the data port 614, the short-range communications subsystem 622, or any other suitable device subsystem 624. This flexibility in application installation increases the functionality of the wireless-enabled device 102 and may provide enhanced on-device functions, communication-related functions, or both. For example, secure communication applications may enable electronic commerce functions and other such financial transactions to be performed using the wireless-enabled device 102.

The data port 614 enables a subscriber to set preferences through an external device or software application and extends the capabilities of the wireless-enabled device 102 by providing for information or software downloads to the wireless-enabled device 102 other than through a wireless communication network. The alternate download path may, for example, be used to load an encryption key onto the wireless-enabled device 102 through a direct and thus reliable and trusted connection to provide secure device communication.

The data port 614 can be any suitable port that enables data communication between the wireless-enabled device 102 and another computing device. The data port 614 can be a serial or a parallel port. In some instances, the data port 614 can be a USB port that includes data lines for data transfer and a supply line that can provide a charging current to charge the battery 630 of the wireless-enabled device 102.

The short-range communications subsystem 622 provides for communication between the wireless-enabled device 102 and different systems or devices, without the use of the wireless network 605. For example, the subsystem 622 may include an infrared device and associated circuits and components for short-range communication. Examples of short-range communication standards include standards developed by the Infrared Data Association (IrDA), Bluetooth, and the 802.11 family of standards developed by IEEE.

In use, a received signal such as a text message, an e-mail message, web page download, media content, etc. will be processed by the communication subsystem 604 and input to the main processor 602. The main processor 602 will then process the received signal for output to the display 610 or alternatively to the auxiliary I/O subsystem 612. A subscriber may also compose data items, such as e-mail messages, for example, using the keyboard 616 in conjunction with the display 610 and possibly the auxiliary I/O subsystem 612. The auxiliary subsystem 612 may include devices such as: a touch screen, mouse, track ball, infrared fingerprint detector, or a roller wheel with dynamic button pressing capability. The keyboard 616 is preferably an alphanumeric keyboard and/or telephone-type keypad. However, other types of keyboards may also be used. A composed item may be transmitted over the wireless network 605 through the communication subsystem 604.

For voice communications, the overall operation of the wireless-enabled device 102 is substantially similar, except that the received signals are output to the speaker 618, and signals for transmission are generated by the microphone 620. Alternative voice or audio I/O subsystems, such as a voice message recording subsystem, can also be implemented on the wireless-enabled device 102. Although voice or audio signal output is accomplished primarily through the speaker 618, the display 610 can also be used to provide additional information such as the identity of a calling party, duration of a voice call, or other voice call related information.

FIGS. 7A, 7B, 8A, and 8B depict example flow diagrams representative of processes that may be implemented using, for example, computer readable instructions stored on a computer-readable medium to implement bio-certification processes to establish wireless connections between wireless-enabled devices. The example processes of FIGS. 7A, 7B, 8A, and 8B may be performed using one or more processors, controllers, and/or any other suitable processing devices. For example, the example processes of FIGS. 7A, 7B, 8A, and 8B may be implemented using coded instructions (e.g., computer readable instructions) stored on one or more tangible computer readable media such as flash memory, read-only memory (ROM), and/or random-access memory (RAM). As used herein, the term tangible computer readable medium is expressly defined to include any type of computer readable storage and to exclude propagating signals. Additionally or alternatively, the example processes of FIGS. 7A, 7B, 8A, and 8B may be implemented using coded instructions (e.g., computer readable instructions) stored on one or more non-transitory computer readable media such as flash memory, read-only memory (ROM), random-access memory (RAM), cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIGS. 7A, 7B, 8A, and 8B may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 7A, 7B, 8A, and 8B may be implemented manually or as any combination(s) of any of the foregoing techniques, for example, any combination of firmware, software, discrete logic and/or hardware. Further, although the example processes of FIGS. 7A, 7B, 8A, and 8B are described with reference to the flow diagrams of FIGS. 7A, 7B, 8A, and 8B, other methods of implementing the processes of FIGS. 7A, 7B, 8A, and 8B may be employed. For example, the order of execution of the blocks may be changed, and/or some of the blocks described may be changed, eliminated, sub-divided, or combined. Additionally, any or all of the example processes of FIGS. 7A, 7B, 8A, and 8B may be performed sequentially and/or in parallel by, for example, separate processing threads, processors, devices, discrete logic, circuits, etc.

Figure 7A:
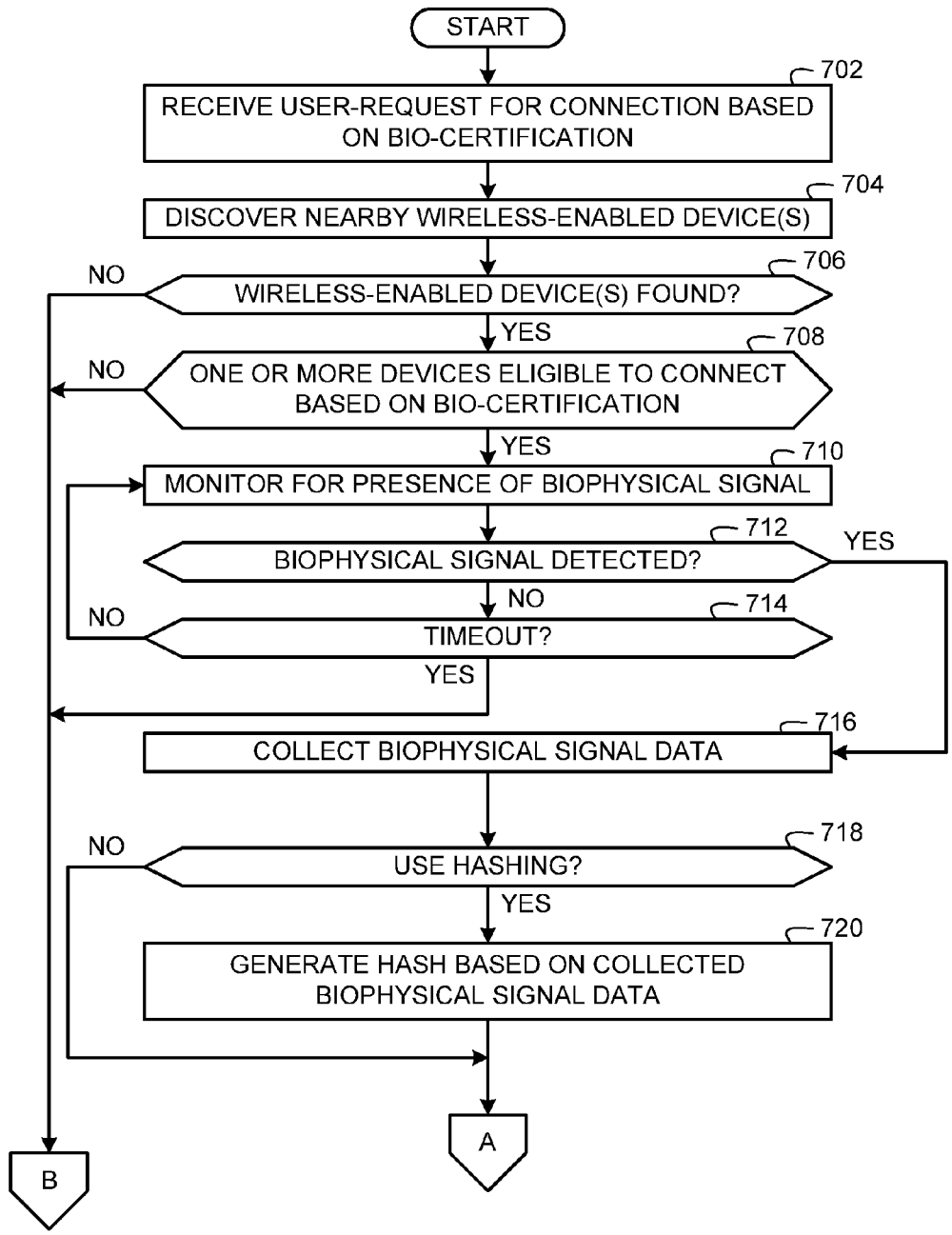
FIGS. 7A and 7B depict an example flow diagram representative of computer readable instructions that may be used to initiate a bio-certification process to establish a wireless connection between two wireless-enabled devices.
Figure 7B:
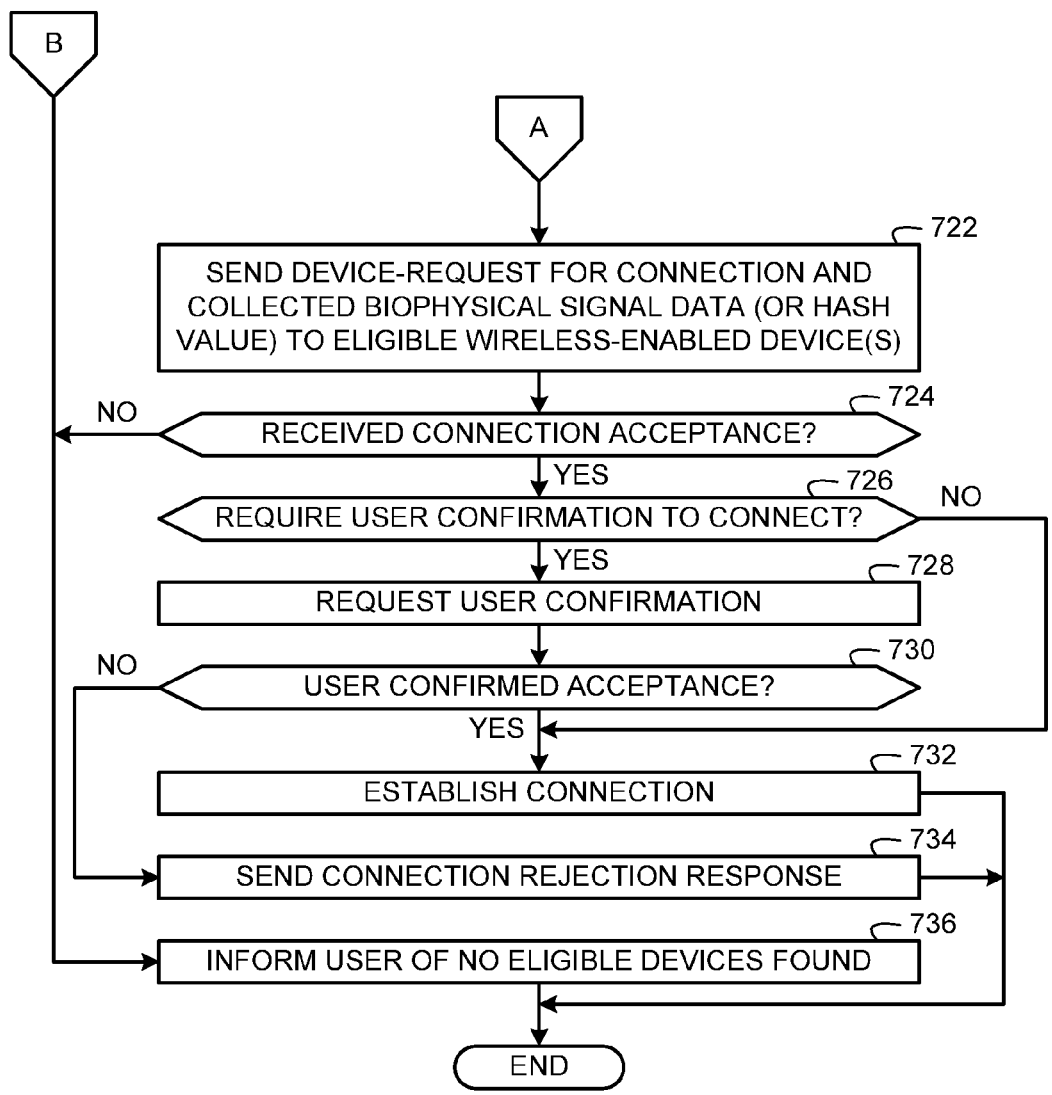

Now turning to FIGS. 7A and 7B, the depicted flow diagram is representative of an example process that may be used to initiate a bio-certification process to establish a wireless connection between two wireless-enabled devices. The example process is described below as being performed by the wireless-enabled device 102 as implemented using the apparatus 500 of FIG. 5 to establish a wireless connection (e.g., the wireless connection 114 of FIG. 1) with the wireless-enabled device 104. However, the example process may alternatively be performed by the wireless-enabled device 104 and/or the wireless-enabled headphones 106 (or any other device) to establish a wireless connection with the wireless-enabled device 102 (or any other device).

Referring to FIG. 7A, initially, the wireless-enabled device 102 receives a user-request to establish a wireless connection (e.g., the wireless connection 114 of FIG. 1) using a bio-certification process (block 702). For example, the person 100 of FIG. 1 may press the button 204 or select the icon 208 of FIG. 2 (and/or pick up/hold/touch the wireless-enabled device 102 to engage the sensor 202 of FIG. 2) to initiate a bio-certification process.

The wireless-enabled device 102 performs a discovery process to discover nearby wireless-enabled device(s) (block 704). For example, the wireless-enabled device 102 may use one of the communication interfaces 510 to perform a device discovery process (e.g., a Bluetooth® discovery process) to discover one or both of the wireless-enabled device 104 and/or the wireless-enabled headphones 106 of FIG. 1.

The wireless-enabled device 102 determines whether it found any other wireless-enabled device(s) (block 706). If the wireless-enabled device 102 does not find any other wireless-enabled device(s), control advances to block 736 of FIG. 7B.

If the wireless-enabled device 102 finds at least one wireless-enabled device (e.g., the wireless-enabled device 104 of FIG. 1) (block 706), the connection arbiter 504 (FIG. 5) determines whether one or more of the discovered devices is/are eligible to connect using a bio-certification process (block 708). For example, the connection arbiter 504 can access a listing in the configuration data store 502 (FIG. 5) indicative of devices approved for bio-certification. If the connection arbiter 504 determines that no discovered devices is/are eligible to connect using a bio-certification process, control advances to block 736 of FIG. 7B.

If the connection arbiter 504 determines that at least one of the discovered devices is approved for establishing wireless connections based on bio-certification processes (block 708), control advances to block 710, at which the biophysical signal data collector 506 (FIG. 5) monitors for the presence of a biophysical signal (e.g., the biophysical signals 110 of FIG. 1) (block 710).

If a biophysical signal 110 is not detected (block 712), the connection arbiter 504 determines whether a timeout has been reached (block 714). For example, the connection arbiter 504 may start a timeout timer providing sufficient time within which the biophysical signal data collector 506 should detect a biophysical signal 110 before timing out and informing a user that a wireless connection cannot be established because biophysical signals have not been detected. When the timeout has not expired at block 714, control returns to the example operations of blocks 710 and 712 to determine whether the biophysical signal data collector 506 has detected a biophysical signal 110. When the timeout has expired at block 714, control advances to block 736 of FIG. 7B.

When the biophysical signal data collector 506 has detected a biophysical signal 110 (block 712), control advances to block 716, at which the biophysical signal data collector 506 collects biophysical signal data (e.g., the biophysical signal data 112 of FIG. 1) (block 716). The encryption codec 512 (FIG. 5) determines whether to use hashing to request a wireless connection (block 718). For example, the configuration data store 502 may store preferences or settings indicating whether hashing or encryption techniques should be used during bio-certification processes to establish wireless connections. If the encryption codec 512 determines that it should not use hashing, control advances to block 722 of FIG. 7B.

If the encryption codec 512 determines that it should use hashing, the encryption codec 512 generates a hash value based on the biophysical signal data collected at block 716 (block 720). In the illustrated example, the encryption codec 512 uses the biophysical signal data 112 collected at the wireless-enabled device 102 as a private key to generate a hash of public or shared information (e.g., a value or information that is known to all wireless-enabled devices).

After generating the hash value at block 720 or if the encryption codec 512 determines at block 718 that it should not use hashing, the wireless-enabled device 102 sends a device-request for a wireless connection and the collected biophysical signal data 112 (or a hash value generated at block 720) to eligible ones of the wireless-enabled devices identified at block 708 (block 722) (FIG. 7B). In the illustrated example, the wireless-enabled device 102 uses one of the communication interfaces 510 (FIG. 5) to send the device-request and the collected biophysical signal data 112 to the wireless-enabled device 104 via a broadcast channel or any other channel (e.g., an open channel) suitable for sending such a communication. In some examples, the wireless-enabled device 102 is not configured to generate hash values. In such some examples, the operations of blocks 718 and 720 may be omitted, and control advances from block 716 to block 722.

After a predetermined amount of time has passed, the connection arbiter 504 determines whether it has received a connection acceptance message (block 724) from, for example, the wireless-enabled device 104. In the illustrated example, the connection arbiter 504 will receive a connection acceptance message from the wireless-enabled device 104 if the wireless-enabled device 104 has locally collected biophysical signal data 113 and confirmed a sufficient match between the locally collected biophysical signal data 113 and the biophysical signal data 112 received from the wireless-enabled device 102. An example process that may be implemented by the wireless-enabled device 104 to perform biophysical signal data comparisons is described below in connection with the example flow diagram of FIGS. 8A and 8B. In some instances, a user will be in contact with only two wireless-enabled devices, one of which is the wireless-enabled device 102 that initiates and sends the device-request at block 722. During such instances, the wireless-enabled device 102 typically will receive a connection acceptance from only one wireless-enabled device (e.g., the wireless-enabled device 104). However, if the wireless-enabled device 102 receives connection acceptance messages from more than one wireless-enabled device (e.g., the wireless-enabled device 104 and the wireless-enabled headphones 106 of FIG. 1), the wireless-enabled device 102 may present a dialog message (e.g., via the display 610 of FIG. 6) to a user requesting the user to select a device with which to continue the bio-certification process to establish a wireless connection. In this manner, the wireless-enabled device 102 may ignore connection acceptance messages received from non-selected device(s). If the connection arbiter 504 determines that it has not received a connection acceptance message, control advances to block 736.

If the connection arbiter 504 determines that it has received a connection acceptance message (block 724), the connection arbiter 504 determines whether user confirmation is required to connect with the wireless-enabled device 104 (block 726). For example, the connection arbiter 504 can access a listing in the configuration data store 502 (FIG. 5) indicative of devices that require user-confirmation prior to allowing or permitting a wireless connection. If the connection arbiter 504 determines that user confirmation is not required to connect with the wireless-enabled device 104, control advances to block 732.

If the connection arbiter 504 determines that user confirmation is required to connect with the wireless-enabled device 104, the connection arbiter 504 requests a user confirmation (block 728). In the illustrated example, the connection arbiter 504 causes the wireless-enabled device 102 to present a message (e.g., via the display 610 of FIG. 6) similar to the GUI message 400 of FIG. 4 to request user confirmation that it is ok to establish a wireless connection (e.g., the wireless connection 114 of FIG. 1) with the wireless-enabled device 104.

If at block 730 the connection arbiter 504 receives a user confirmation accepting the establishing of the wireless connection 114, the connection arbiter 504 allows or permits the establishing of the wireless connection 114 and control advances to block 732.

At block 732, the wireless-enabled device 102 establishes the wireless connection 114 with the wireless-enabled device 104 via, for example, one of the communication interfaces 510.

Returning to block 730, if the connection arbiter 504 determines that a user did not confirm acceptance to establish the wireless connection 114, control advances to block 734, at which the wireless-enabled device 102 sends a connection rejection response to the wireless-enabled device 104 via, for example, one of the communication interfaces 510. In some examples, when the user does not confirm acceptance to establish the wireless connection 114, the wireless-enabled device 102 may ignore the connection acceptance message received at block 724 instead of sending the rejection response at block 734.

At block 736, the wireless-enabled device 102 informs a user (e.g., the person 100 of FIG. 1) that no eligible devices with which to establish a wireless connection were found (block 736).

After informing a user that no eligible devices were found (block 736), or after sending a connection rejection response (block 734), or after establishing the wireless connection 114 (block 732), the example process of FIGS. 7A and 7B is ended.

Figure 8A:
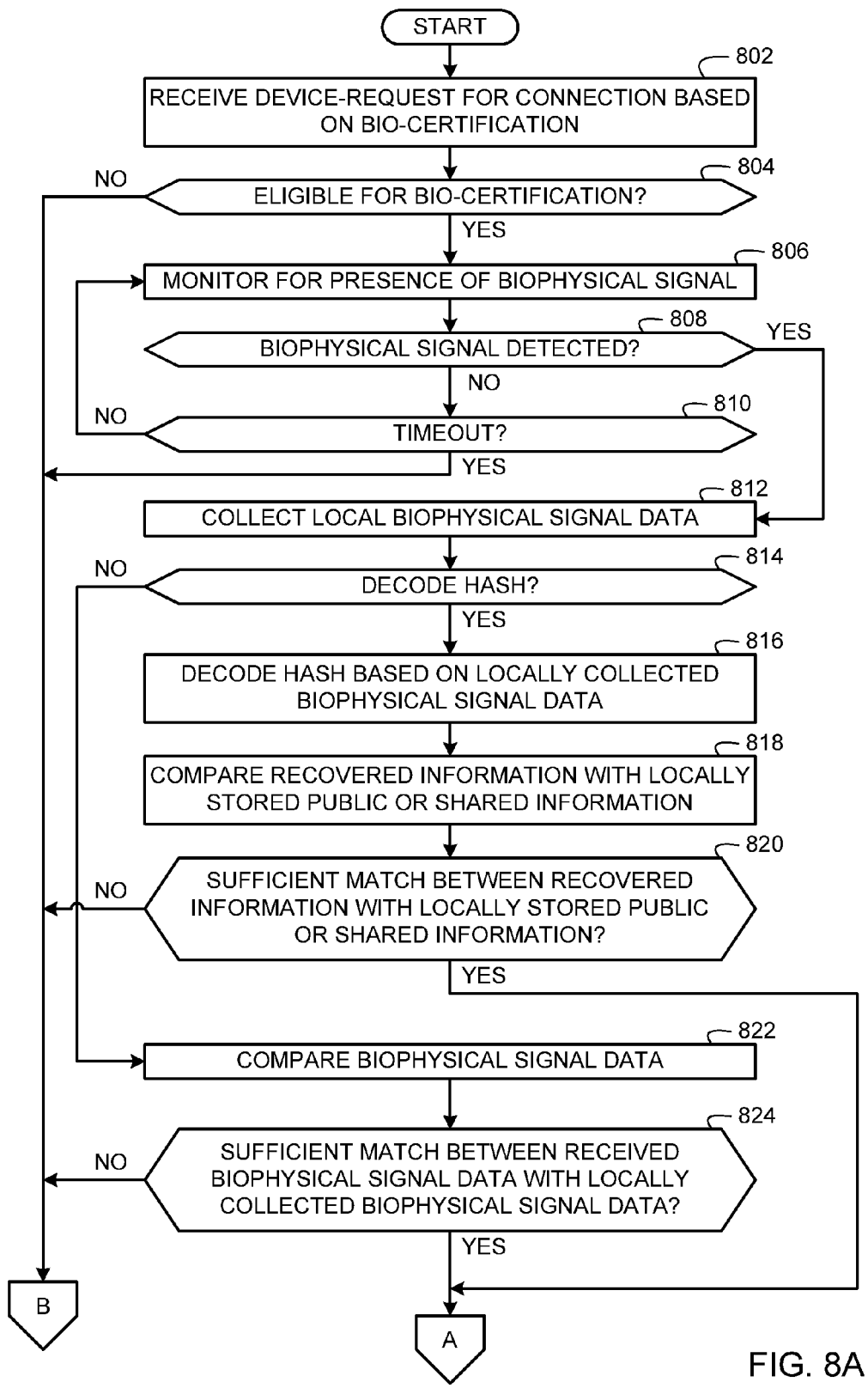
FIGS. 8A and 8B depict an example flow diagram representative of computer readable instructions that may be used to receive a request from a wireless-enabled device to establish a wireless connection based on a bio-certification process.
Figure 8B:
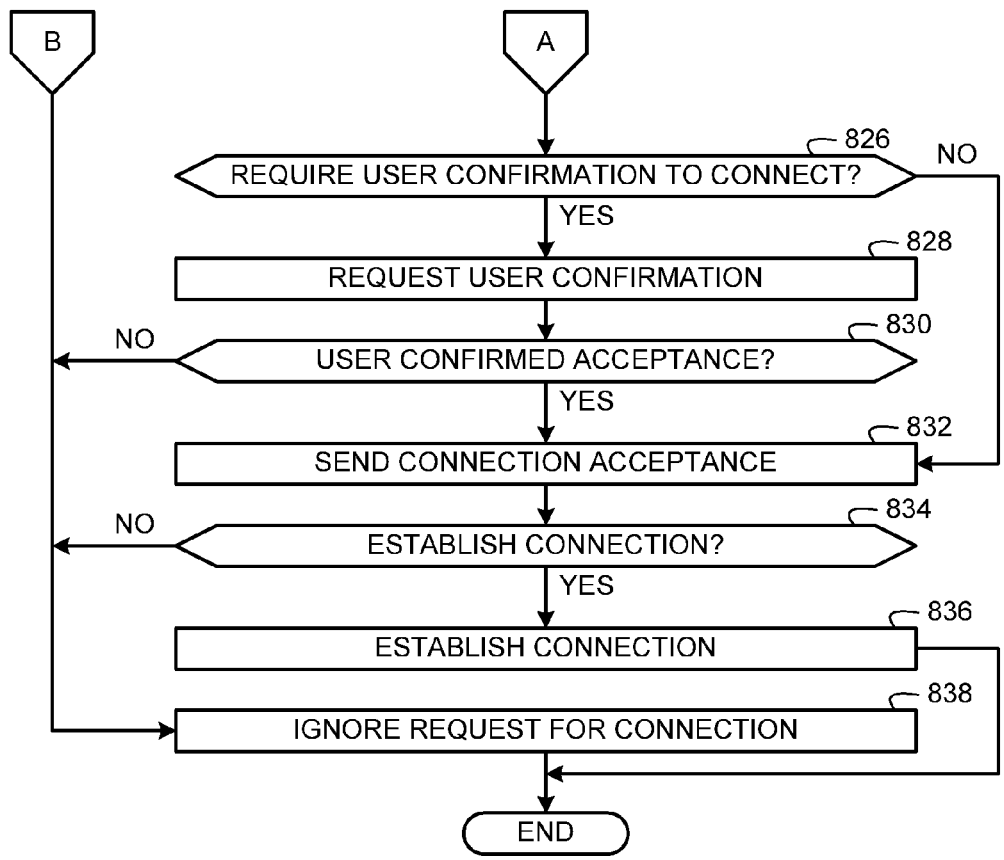

Now turning to FIGS. 8A and 8B, the depicted flow diagram is representative of an example process that may be implemented by a wireless-enabled device (e.g., the wireless-enabled device 104 or the wireless-enabled headphones 106 of FIG. 1) to receive a request from another wireless-enabled device (e.g., the wireless-enabled device 102 of FIG. 1) to establish a wireless connection (e.g., the wireless connection 114 of FIG. 1) based on a bio-certification process. Although the example process is described as being performed by the wireless-enabled device 104 as implemented using an apparatus substantially similar or identical to the example apparatus 500 of FIG. 5, the example process may instead be performed by any other device (e.g., the wireless-enabled device 102 and/or the wireless-enabled headphones 106 of FIG. 1). In the illustrated example, the example process of FIGS. 8A and 8B is performed by the wireless-enabled device 104 in response to receiving a device-request for connection sent by the wireless-enabled device 102 at block 722 of the example process of FIGS. 7A and 7B.

Referring to FIG. 8A, initially, the wireless-enabled device 104 receives a device-request for connection based on bio-certification (block 802). In the illustrated example, the wireless-enabled device 104 receives the device-request for connection sent by the wireless-enabled device 102 at block 722 of the example process of FIGS. 7A and 7B. At block 802, the wireless-enabled device 104 also receives the biophysical signal data 112 (or a hash value generated at block 720 of FIG. 7A).

The wireless-enabled device 104 determines whether it is eligible for establishing a wireless connection (e.g. the wireless connection 114) with the wireless-enabled device 102 based on bio-certification (block 804). For example, the wireless-enabled device 104 may use its connection arbiter 504 of FIG. 5 to access a listing in its configuration data store 502 (FIG. 5) indicative of devices approved for bio-certification. If the wireless-enabled device 104 determines that it is not eligible for establishing a wireless connection with the wireless-enabled device 102 based on bio-certification, control advances to block 838 of FIG. 8B, where the wireless-enabled device 104 ignores the device-request for connection received at block 802.

If the connection arbiter 504 determines that the wireless-enabled device 102 is approved for connecting with based on bio-certification (block 804), the wireless-enabled device 104 monitors for the presence of a biophysical signal 110 (FIG. 1) (block 806). For example, the wireless-enabled device 104 may use its biophysical signal data collector 506 to determine whether it can detect a biophysical signal 110.

If a biophysical signal 110 is not detected (block 808), the connection arbiter 504 determines whether a timeout has been reached (block 810). For example, the connection arbiter 504 may start a timeout timer providing sufficient time within which the biophysical signal data collector 506 should detect a biophysical signal 110 before timing out. When the timeout has not expired at block 810, control returns to the example operations of blocks 806 and 808 to determine whether the biophysical signal data collector 506 has detected a biophysical signal 110. When the timeout has expired at block 810, control advances to block 838 of FIG. 8B.

When the biophysical signal data collector 506 has detected a biophysical signal 110 (block 808), control advances to block 812, at which the biophysical signal data collector 506 collects local biophysical signal data (e.g., the locally collected biophysical signal data 113 of FIG. 1) (block 812).

The encryption codec 512 (FIG. 5) determines whether to decode a hash (block 814). For example, if the encryption codec 512 receives a hash value (e.g., a hash value generated at block 720 of FIG. 7A) from the device-request for connection received at block 802, the encryption codec 512 determines at block 814 that it should decode the received hash. Otherwise, if no hash value was received at block 802, then the encryption codec 512 need not decode a hash.

If the encryption codec 512 does determine at block 814 that it should decode a hash, the encryption codec 512 decodes a hash received at block 802 based on the locally collected biophysical signal data 113 collected at block 812 (block 816). In the illustrated example, the encryption codec 512 uses the locally collected biophysical signal data 113 collected at the wireless-enabled device 104 as a private key to decode the hash and recover information hashed therein. If the locally collected biophysical signal data 113 corresponds to the same person (e.g., the person 100 of FIG. 1) that is associated with the biophysical signal data 112 as shown in FIG. 1, the encryption codec 512 will recover, at block 816, the public or shared information (e.g., a value or information that is known to all wireless-enabled devices) that the wireless-enabled device 102 hashed at block 720 of FIG. 7A. If the locally collected biophysical signal data 113 does not correspond to the same person that is associated with the biophysical signal data 112, then the encryption codec 512 will recover, at block 816, information that is different from the public or shared information that the wireless-enabled device 102 hashed at block 720 of FIG. 7A.

After decoding the hash at block 816, the comparator 508 compares the recovered information with locally stored public or shared information (e.g., a value or information that is known to all wireless-enabled devices) (block 818).

The connection arbiter 504 determines whether there is a sufficient match (e.g., a match within an acceptable tolerance or threshold based on, for example, a matching score) between the recovered information (i.e., the information recovered at block 816) and the locally stored public or shared information (block 820). If a sufficient match is found at block 820, control advances to block 826 shown in FIG. 8B. If a sufficient match is not found at block 820, control advances to block 838 of FIG. 8B.

Returning to block 814, if the encryption codec 512 determines that it should not decode a hash (e.g., a hash was not received at block 802), control advances from block 814 to block 822. In some examples, the wireless-enabled device 104 is not configured to monitor for hash values or decode hash values. In such some examples, the operations of blocks 814, 816, 818, and 820 may be omitted, and control advances from block 812 to block 822.

At block 822, the wireless-enabled device 104 uses its comparator 508 (FIG. 5) to compare the biophysical signal data 112 received at block 802 with the locally collected biophysical signal data 113 (block 822).

The connection arbiter 504 determines whether there is a sufficient match between the received biophysical signal data 112 and the locally collected biophysical signal data 113 (block 824). The connection arbiter 504 may determine whether a sufficient match exists based on a comparison score generated by the comparator 508 and a matching score threshold as described above in connection with FIG. 5. If a sufficient match is not found at block 824, control advances to block 838 of FIG. 8B.

If a sufficient match is found at block 824 or at block 820, the wireless-enabled device 104 uses its connection arbiter 504 to determine whether user confirmation is required to connect with the wireless-enabled device 102 (block 826) (FIG. 8B). For example, the connection arbiter 504 can access a listing in the configuration data store 502 (FIG. 5) of the wireless-enabled device 104 indicative of devices that require user-confirmation prior to allowing a wireless connection. If the connection arbiter 504 determines that user confirmation is not required to connect with the wireless-enabled device 102, control advances to block 832.

If the connection arbiter 504 determines that user confirmation is required to connect with the wireless-enabled device 102, the connection arbiter 504 requests a user confirmation (block 828). In the illustrated example, the connection arbiter 504 causes the wireless-enabled device 104 to present a message (e.g., via the display 610 of FIG. 6) similar to the GUI message 400 of FIG. 4 to request user confirmation indicating that it is ok to establish a wireless connection (e.g., the wireless connection 114 of FIG. 1) with the wireless-enabled device 102.

If at block 830 the connection arbiter 504 receives a user confirmation accepting the establishing of the wireless connection 114, control advances to block 832. If at block 830 the connection arbiter 504 does not receive a user confirmation accepting the establishing of the wireless connection 114, control advances to block 838.

At block 832, the wireless-enabled device 104 sends a connection acceptance message via one of its communication interfaces 510 (FIG. 5) to the wireless-enabled device 102. In the illustrated example, the connection acceptance message sent by the wireless-enabled device 104 is the connection acceptance message received by the wireless-enabled device 102 at block 724 of FIG. 7B.

The connection arbiter 504 of the wireless-enabled device 104 then determines whether it should establish the wireless connection 114 (block 834). For example, the connection arbiter 504 may establish the wireless connection 114 if it receives an acceptance or negotiation from the wireless-enabled device 102 to successfully establish the wireless connection 114 (e.g., see the operation of block 732 of FIG. 7B at which the wireless-enabled device 102 proceeds to successfully establish the wireless connection 114). If the connection arbiter 504 determines at block 834 that it should allow or permit the wireless connection 114, the wireless-enabled device 104 establishes the wireless connection 114 with the wireless-enabled device 102 via, for example, one of the communication interfaces 510 (block 836).

If at block 834 the wireless-enabled device 104 receives a connection rejection response from the wireless-enabled device 102 (e.g., see block 734 of FIG. 7B) or does not receive any response or further negotiation from the wireless-enabled device 102, the connection arbiter 504 determines that it should not allow the wireless connection 114 and control advances to block 838.

At block 838, the wireless-enabled device 104 ignores the device-request for connection received at block 802 (block 838). After ignoring the device-request for connection at block 838 or after establishing the wireless connection 114 at block 836, the example process of FIGS. 8A and 8B ends.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

What is claimed is:

1. A method of establishing a connection between wireless-enabled devices, comprising:
    collecting first biophysical signal data via a first wireless-enable device in response to receiving a user request to establish a wireless connection based on the matching of the first biophysical signal data and second biophysical signal data; and
    establishing the wireless connection between the first wireless-enable device and a second wireless-enabled device based on a comparison of the first biophysical signal data and the second biophysical signal data collected at the second wireless-enabled device.

2. The method as defined in claim 1, further comprising, prior to establishing the wireless connection, sending the first biophysical signal data to the second wireless-enabled device and comparing the first biophysical signal data and the second biophysical signal data at the second wireless-enabled device.

3. The method as defined in claim 1, wherein the first biophysical signal data is representative of a biophysical signal of a person in contact with the first wireless-enabled device.

4. The method as defined in claim 3, wherein the biophysical signal is a heart rate of the person.

5. The method as defined in claim 1, further comprising, prior to establishing the wireless connection, confirming that the first wireless-enabled device is eligible to establish the wireless connection with the second wireless-enabled device using a process that compares the first and second biophysical signal data.

6. A method of establishing a wireless connection between wireless-enabled devices, comprising:
    determining whether user confirmation is required to permit the establishing of the wireless connection;
    when the establishing of the wireless connection requires the user confirmation, requesting a user to confirm acceptance to establish the wireless connection;
    collecting first biophysical signal data via a first wireless-enabled device; and
    establishing the wireless connection between the first wireless-enabled device and a second wireless-enabled device, based on a comparison of the first biophysical signal data and second biophysical signal data collected at the second wireless-enabled device, when the user confirms acceptance to permit the establishing of the wireless connection.

7. The method as defined in claim 6, wherein a requirement of the user confirmation to establish the wireless connection is indicated in a configuration data store of the first wireless-enabled device.

8. An apparatus for establishing a connection between wireless-enabled devices, comprising:
    a processor; and
    a memory in communication with the processor having instructions stored thereon that, when executed, cause the processor to:
        determine whether user confirmation is required to permit the establishing of the wireless connection;
        when the establishing of the wireless connection requires the user confirmation, request a user to confirm acceptance to establish the wireless connection;
        collect first biophysical signal data via a first wireless-enabled device; and compare the first biophysical signal data to second biophysical signal data received from a second wireless-enabled device;

establish the wireless connection between the first wireless-enabled device and the second wireless-enabled device, based on the comparison of the first biophysical signal data to the second biophysical signal data, when the user confirms acceptance to permit the establishing of the wireless connection.

9. The apparatus as defined in claim 8, wherein a requirement of the user confirmation to establish the wireless connection is indicated in a configuration data store of the first wireless-enabled device.

10. An apparatus for establishing a connection between wireless-enabled devices, comprising:
a processor; and
a memory in communication with the processor having instructions stored thereon that, when executed, cause the processor to:
collect first biophysical signal data via a first wireless-enabled device in response to receiving a user request to establish a wireless connection based on the first biophysical signal data matching second biophysical signal data;
compare the first biophysical signal data to the second biophysical signal data received from a second wireless-enabled device; and
establish the wireless connection between the first and second wireless-enabled devices based on the comparison of the first biophysical data to the second biophysical signal data.

11. The apparatus as defined in claim 10, wherein the first biophysical signal data is representative of a biophysical signal of a person in contact with the first wireless-enabled device.

12. The apparatus as defined in claim 11, wherein the biophysical signal is a heart rate of the person.

13. The apparatus as defined in claim 10, wherein the instructions, when executed, further cause the processor to generate a matching score based on the comparison of the first and second biophysical signal data, the wireless connection being established when the matching score exceeds a matching score threshold associated with an inexact match.

14. The apparatus as defined in claim 10, wherein the instructions, when executed, further cause the processor to, prior to establishing the wireless connection, confirm that the first wireless-enabled device is eligible to establish the wireless connection with the second wireless-enabled device based on the first and second biophysical signal data.

15. The apparatus as defined in claim 10, wherein the collecting of the first biophysical signal data at the first wireless-enabled device is performed after receiving the second biophysical signal data from the second wireless-enabled device.

16. An apparatus for establishing a connection between wireless-enabled devices, comprising:
a comparator to compare first biophysical signal data collected at a first wireless-enabled device to second biophysical signal data collected at a second wireless-enabled device after receiving a user request to establish a wireless connection based on the first biophysical signal data matching the second biophysical signal data; and
a connection arbiter to permit establishing a wireless connection between the first and second wireless-enabled devices based on a comparison of the first biophysical signal data to the second biophysical signal data.

17. The apparatus as defined in claim 16, further comprising a biophysical signal data collector to collect the first biophysical signal data at the first wireless-enabled device.

18. The apparatus as defined in claim 17, wherein the biophysical signal data collector is connected to a sensor configured to engage a person to detect biophysical signals of the person.

19. The apparatus as defined in claim 16, wherein the biophysical signal data corresponds to a heart rate of a person in contact with at least one of the first wireless-enabled device or the second wireless-enabled device.

20. A tangible computer readable medium having instructions stored thereon that, when executed, cause a machine to at least:
collect first biophysical signal data via a first wireless-enabled device in response to receiving a user request to establish a wireless connection based on the first biophysical signal data matching second biophysical signal data; and
establish the wireless connection between the first wireless-enabled device and a second wireless-enabled device based on a comparison of the first biophysical signal data and the second biophysical signal data collected at the second wireless-enabled device.

21. The tangible computer readable medium as defined in claim 20, wherein the instructions cause the machine to, prior to establishing the wireless connection, send the first biophysical signal data to the second wireless-enabled device to compare the first biophysical signal data and the second biophysical signal data at the second wireless-enabled device.

22. The tangible computer readable medium as defined in claim 20, wherein the first biophysical signal data is representative of a biophysical signal of a person in contact with the first wireless-enabled device.

23. The tangible computer readable medium as defined in claim 22, wherein the biophysical signal is a heart rate of the person.

24. The tangible computer readable medium as defined in claim 20, wherein the instructions cause the machine to, prior to establishing the wireless connection, confirm that the first wireless-enabled device is eligible to establish the wireless connection with the second wireless-enabled device using a process that compares the first and second biophysical signal data.

* * * * *